(12) United States Patent
Bolli et al.

(10) Patent No.: US 8,658,675 B2
(45) Date of Patent: Feb. 25, 2014

(54) PYRIDIN-4-YL DERIVATIVES

(75) Inventors: Martin Bolli, Allschwil (CH); Cyrille Lescop, Allschil (CH); Boris Mathys, Allschwil (CH); Keith Morrison, Allschwil (CH); Claus Mueller, Allschwil (CH); Oliver Nayler, Allschwil (CH); Beat Steiner, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 41 days.

(21) Appl. No.: 13/383,619

(22) PCT Filed: Jul. 15, 2010

(86) PCT No.: PCT/IB2010/053224
§ 371 (c)(1),
(2), (4) Date: Jan. 12, 2012

(87) PCT Pub. No.: WO2011/007324
PCT Pub. Date: Jan. 20, 2011

(65) Prior Publication Data
US 2012/0108638 A1  May 3, 2012

(30) Foreign Application Priority Data
Jul. 16, 2009  (WO) .................. PCT/IB2009/053089

(51) Int. Cl.
C07D 413/04  (2006.01)

(52) U.S. Cl.
USPC ........................................ 514/340; 546/269.4

(58) Field of Classification Search
None
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 | 10/2009 | Colandrea et al. | |
| 7,605,269 B2 | 10/2009 | Bolli et al. | |
| 7,723,378 B2 | 5/2010 | Bolli et al. | |
| 7,750,040 B2 | 7/2010 | Bolli et al. | |
| 7,834,039 B2 | 11/2010 | Hobson et al. | |
| 7,846,964 B2 | 12/2010 | Bolli et al. | |
| 7,951,794 B2 | 5/2011 | Bolli et al. | |
| 8,003,800 B2 | 8/2011 | Bolli et al. | |
| 8,044,076 B2 | 10/2011 | Bolli et al. | |
| 8,133,910 B2 | 3/2012 | Bolli et al. | |
| 8,148,410 B2 | 4/2012 | Bolli et al. | |
| 8,288,554 B2 * | 10/2012 | Bolli et al. | 546/268.7 |
| 8,299,086 B2 | 10/2012 | Bolli et al. | |
| 2007/0021443 A1 | 1/2007 | Ohlmeyer et al. | |
| 2007/0043104 A1 | 2/2007 | Luthman et al. | |
| 2007/0270438 A1 | 11/2007 | Bhattacharya et al. | |
| 2008/0064740 A1 | 3/2008 | Bolli et al. | |
| 2008/0113961 A1 | 5/2008 | Nishi et al. | |
| 2008/0249093 A1 | 10/2008 | Colandrea et al. | |
| 2008/0300294 A1 | 12/2008 | Bolli et al. | |
| 2008/0306124 A1 | 12/2008 | Albert et al. | |
| 2009/0005421 A1 | 1/2009 | Bolli et al. | |
| 2009/0275554 A1 | 11/2009 | Habashita et al. | |
| 2010/0048648 A1 | 2/2010 | Bolli et al. | |
| 2010/0063108 A1 * | 3/2010 | Bolli et al. | 514/342 |
| 2010/0075946 A1 | 3/2010 | Bolli et al. | |
| 2010/0087417 A1 | 4/2010 | Bolli et al. | |
| 2010/0087495 A1 | 4/2010 | Bolli et al. | |
| 2010/0168005 A1 | 7/2010 | Bolli et al. | |
| 2010/0234346 A1 | 9/2010 | Bolli et al. | |
| 2010/0240717 A1 | 9/2010 | Boli et al. | |
| 2010/0331372 A1 | 12/2010 | Bolli et al. | |
| 2011/0028448 A1 | 2/2011 | Bolli et al. | |
| 2011/0028449 A1 | 2/2011 | Bolli et al. | |
| 2011/0046170 A1 | 2/2011 | Bolli et al. | |
| 2011/0207704 A1 | 8/2011 | Cusack et al. | |
| 2011/0212998 A1 | 9/2011 | Bolli et al. | |

FOREIGN PATENT DOCUMENTS

| | | |
|---|---|---|
| DE | 10237883 | 3/2004 |
| EP | 0476646 | 3/1992 |
| EP | 0702003 | 6/1998 |
| EP | 1873153 | 1/2008 |
| JP | 2008120794 | 5/2008 |
| WO | WO 91/15583 | 10/1991 |
| WO | WO 99/46277 | 9/1999 |
| WO | WO 00/45799 | 8/2000 |
| WO | WO 01/12627 | 2/2001 |
| WO | WO 02/068417 | 9/2002 |

(Continued)

OTHER PUBLICATIONS

Abhandlung; "Stickstoffhaltige Derivate der Mkonsaure and ihre Umwandlung in Pyridin"; Journal fur Prkitsche Chemie, vol. 27, pp. 257-294 (1883).

Alvernhe et al; Synthesis and Reactivity of 3-chloro-3-trifluoromethylacroleins: Stabilization of the Tetrahedral Intermediate in a Nucleophilic Vinylic "Substitution"; Bull. Soc. Chim. Fr.; 131, 1994, 167-172.

Biyouki et al., Synthetic Communications, vol. 28, pp. 3817-3825 (1989).

Bode et al; "Immune Regulation, Etc."; Arch. Immunol. Ther. Exp.; 60: 3-12; (2012).

Burstein et al; "Imidazo[1,5-a]pyridine-3-ylidenes-pyridine derived N-heterocyclic carbine ligands", Tetrahedron, vol. 61, pp. 6207-6217; (2004).

CAPLUS 2000:553399 [WO 2000/045799] 2000.

(Continued)

*Primary Examiner* — Kamal Saeed
(74) *Attorney, Agent, or Firm* — Hoxie & Associates LLC

(57) ABSTRACT

The invention relates to pyridine derivatives of Formula (I), wherein A, $R^1$, $R^2$, $R^3$, and $R^4$ are as described in the description, their preparation and their use as pharmaceutically active compounds. Said compounds particularly act as immunomodulating agents.

Formula (I)

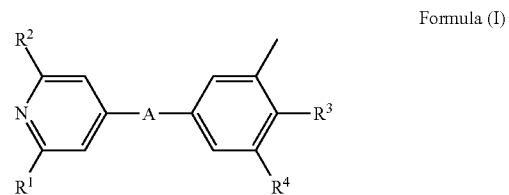

45 Claims, No Drawings

(56) References Cited

FOREIGN PATENT DOCUMENTS

| WO | WO 03/062248 | 7/2003 |
|---|---|---|
| WO | WO 03/062252 | 7/2003 |
| WO | WO 03/105771 | 12/2003 |
| WO | WO 2004/035538 | 4/2004 |
| WO | WO 2004/056789 | 7/2004 |
| WO | WO 2004/103279 | 12/2004 |
| WO | WO 2005/014525 | 2/2005 |
| WO | WO 2005032465 | 4/2005 |
| WO | WO 2005/058848 | 6/2005 |
| WO | WO 2005/115382 | 12/2005 |
| WO | WO 2006/047195 | 5/2006 |
| WO | WO 2006/100631 | 9/2006 |
| WO | WO 2006/114400 | 11/2006 |
| WO | WO 2006/131336 | 12/2006 |
| WO | WO 2007/001973 | 1/2007 |
| WO | WO 2007/085451 | 8/2007 |
| WO | WO 2007/098474 | 8/2007 |
| WO | WO 2007/132307 | 11/2007 |
| WO | WO 2008/029370 | 3/2008 |
| WO | WO 2008/029371 | 3/2008 |
| WO | WO 2008/037476 | 4/2008 |
| WO | WO 2008/076356 | 6/2008 |
| WO | WO 2008/091967 | 7/2008 |
| WO | WO 2009/043889 | 4/2009 |
| WO | WO 2009/043890 | 4/2009 |
| WO | WO 2009/060278 | 5/2009 |
| WO | WO 2009/151529 | 12/2009 |
| WO | WO 2010/148649 | 12/2010 |

OTHER PUBLICATIONS

Comins et al; "Regiospecific a-Alkylation of 4-Chloro(bromo) pyridine"; J. Org. Chem., vol. 50, pp. 4410-4411, (1985).
Cui et al; Design and Synthesis of Highly Constrained Factor Xa Inhibitors: Amidine-Substituted Bis(benzoyl)-[1,3]-diazepan-2-ones and Bis(benzylidene)-bis(gem-dimethyl)Cycloketones, Bioorganic Medicinal Chemistry, 2003, pp. 3379-3392, vol. 11.
Ecke et al; "Ortho-Alkylation of Aromatic Amines"; Journal of Organic Chemistry, 1957, pp. 639-642, vol. 22.
Fallahpour, R. A., Synthesis, No. 12, pp. 1665-1667 (2000).
Finch, N., et al., J. Med. Chem., vol. 23, pp. 1405-1410 (1980).
Furnster et al; "Iron-Catalyzed Cross-coupling Reactions of Alkyl-grignard Reagents with Aryl Chlorides, Tosylates, and Triflates"; Angew. Chem.; 2002; vol. 41, No. 4, pp. 609-612.
Gennaro, "Remington: The Science and Practice of Pharmacy", Table of Contents; 20th Edition, Philadelphia College of Pharmacy and Science 2003.
Gibson (Editor); Pharmaceutical Preformulation and Formulation; HIS Health Group, 2001.
Glennon et al; "B-Oxygenated Analogues of the 5-HT2A Serotonin Receptor Agonist 1-(4Bromo-2,5-dimethoxyphenyl)-2-aminopropane", Journal of Medicinal Chemistry, 2004, pp. 6034-6041, vol. 47.
Golub et al, "Molecular Classification of Cancer: Class Discovery and Class Prediction by Gene Expression Monitoring"; Science, 1999, vol. 286, 531-537.
Gronowitz et al; "On the Synthesis of Branched Saturated Fatty Acids"; Lipids, vol. 28, 1993, 889-897.
Gura; "Systems for Indentifying New Drugs are Often Faulty"; Cancer Models; Science, vol. 278, No. 5340, pp. 1041-1042; Nov. 1997.
Habermehl, N. C., et al., Inorganic Chem., vol. 68, pp. 7316-7321 (2003).
Harris, M.C., J. Org. Chem., vol. 64, pp. 6019-6022 (1999).
Hu et al; "Sphingosine-1-phosphate, etc."; Mol. Biol. Rep.; 38:4225-4230 (2011).
Inouye et al; "Saccharidew-Dependent Induction of Chiral Helicity in Achiral Synthetic Hydrogen-Bonding Oligomers"; J. Am. Chem. Soc., vol. 126; pp. 2022-2027; (2004).
Jo et al; "Spingosine-1-phosphate, Etc."; Kidney International; 73, 1220-1230; (2008).

Johnson et al; "Relationships Between Drug Acitvity in NCI Preclinical In Vitro and In Vivo Models and Early Clinical Trials"; British Journal of Cancer; 64(10): 1524-1431; (2001).
Kaminski T. et al, J. Org. Chem., vol. 19, pp. 3855-3860 (2003).
Katz, R. B. et al., Syn. Communications, vol. 19, pp. 317-325 (1989).
Khlestkin et al; "Recent Advances in the Application of A, O-dialkylhydroxylamines in Organic Chemistry"; Current Organic Chemistry, 7; 2003; 967-993.
Kiryanov et al; "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis"; Journal of Organic Chemistry, 2001, pp. 7925-7929, vol. 66.
Lala et al; "Role of Nitric Oxide in Tumor Progression: Lessons From Experimental Tumors"; Cancer and Metastasis Reviews (1998), 17, 91-106.
Lamattina; "The Synthesis of 2-Amino-4-(4-imidazolyl)pyridines"; J. Heterocyclic Chem.; 20; 1983; 533-538.
Mentzel et al; "N-Methoxy N-methyl amides (Weinred amides) in Modern Organic Synthesis"; Journal fur Praktische Chemie Chiker-Zeitung; 339; 1997; 517-524.
Meyer et al; "Synthesis of New 1,2,4- and 1,3,4-Oxadiazole Derivatives"; Synthesis; 2003; pp. 899-905, No. 6.
Meyer Zu Heringdorf et al; "Pharmacology of the Sphingosine-1-Phosphate Signalling System"; Sphingolipids: Basic Science and Drug Development; Handbook of Experimental Pharmacology 215, pp. 239-253; 2013.
Nguyen et al; "Combined Directed Ortho Metalation/Cross-Coupling Strategies: Synthesis of the Tetracyclic A/B/C/D Ring Core of the Antitumor Agent Camptothecin"; J. Org. Chem., vol. 69, pp. 7816-7821; (2004).
Notice of Allowance dated Jun. 13, 2012 for U.S. Appl. No. 12/310,763.
Notice of Allowance dated Jun. 20, 2012 for U.S. Appl. No. 12/738,110.
Notice of Allowance dated Nov. 18, 2011 for U.S. Appl. No. 12/747,280.
Notice of Allowance dated Nov. 28, 2012 for U.S. Appl. No. 12/920,574.
Notice of Allowance dated Sep. 26, 2011 for U.S. Appl. No. 12/442,203.
Office Action—Final dated Feb. 8, 2013 for U.S. Appl. No. 12/920,656.
Office Action—Final dated Feb. 7, 2013 for U.S. Appl. No. 12/637,918.
Office Action—Final dated Nov. 8, 2012 for U.S. Appl. No. 12/310,801.
Office Action—Restriction dated Jul. 24, 2012 for U.S. Appl. No. 12/920,569.
Office Action—Restriction dated May 24, 2012 for U.S. Appl. No. 12/920,656.
Office Action dated Apr. 26, 2012 for U.S. Appl. No. 12/531,374.
Office Action dated Dec. 2, 2011 for U.S. Appl. No. 12/310,763.
Office Action dated Dec. 2, 2011 for U.S. Appl. No. 12/531,374.
Office Action dated Dec. 6, 2011 for U.S. Appl. No. 12/310,801.
Office Action dated Feb. 17, 2012 for U.S. Appl. No. 12/673,918.
Office Action dated Jan. 3, 2013 for U.S. Appl. No. 12/531,374.
Office Action dated Jan. 4, 2013 for U.S. Appl. No. 12/920,569.
Office Action dated Jun. 11, 2012 for U.S. Appl. No. 12/673,918.
Office Action dated Jun. 27, 2012 for U.S. Appl. No. 12/310,801.
Office Action dated Jun. 7, 2011 for U.S. Appl. No. 12/310,763.
Office Action dated Mar. 1, 2012 for U.S. Appl. No. 12/310,763.
Office Action dated Oct. 31, 2012 for U.S. Appl. No. 12/920,656.
Office Action dated Oct. 8, 2010 for U.S. Appl. No. 12/310,763.
Paine, "A Convenient Synthesis of Nicotinate Esters from 3-cyanopyridones"; J. Heterocyclic; 1987; vol. 24, pp. 351-355.
Patani et al; "Bioisosterism: A Rational Approach in Drug Design"; Chem. Rev. 1996, vol. 96, No. 8, pp. 3147-3176.
Pesson et al; "Antibacteriens de Syntheses—Derives de L'acide Pipemidique"; Eur. J. Med. Chem.; 15; 1980; 263-268.
Pierrat, P. et al., Synlett., No. 13, pp. 2319-2322 (2004).

(56) References Cited

OTHER PUBLICATIONS

Poulain et al; "Parallel Synthesis of 1,2,4-oxadiazoles from Carboxylic Acids Using an Improved , Uronium-based, Activation"; Tetrahedron Letters, 2001, pp. 1495-1498, vol. 42.
Remington, "The Science and Practice of Pharmacy", 21st Edition (2005), Part 5—Table of Contents, "Pharmaceutical Manufacturing", Published by Lippincott Williams & Wilkins.
Roberts et al; "Sphingosine 1-phosphate Receptor Agonists: A Patent Review"; Expert Opionino; The Scripps Research Institute, Dept. of Chemistry; 2013; pp. 1-25.
Robinson; "Medical Therapy of Inflammatory Bowel Disease for the 21st Century"; Eur. J. Sug. 164, Suppl. 582, pp. 90-98 (1998).
Roth et al; "2-4-Diamino-5-benzylyrimidines and Analogs as Antibacterial Agents"; J. Med. Chem.; 1988; vol. 31, No. 1; pp. 122-129.
Sato et al; "Synthesis and Evaluation of Substituted 4-alkoxy-2-aminopyridines as Novel Neuropeptide Y1 Receptor Antagonists", Bioorganic and Medicinal Chemistry Letters, 2004, pp. 1761-1764, vol. 14.
Schurer et al; ACS Chemical Biolog, vol. 3; No. 8; pp. 486-498; 2008.
Silverman; "The Organic Chemistry of Drug Design and Drug Action"; 2004; Elsevier, pp. 29-32.
Silverman; "The Organic Chemistry of Drug Design and Drug Action"; 2004; Elsevier, pp. 9.
Simeone et al; "Modification of the Pyridine Moiety of Non-peptidyl Indole GnRH Receptor Antagonists"; Bioorganic & Medicinal Chemistry Letters; Volo. 12, pp. 3329-3332; (2002).
Simone; "Oncology: Introduction"; Cecil Textbook of Medicine, 20th Edition; vol. 1; pp. 1004-1010; (1996).
Singh et al; "The Growing Synthetic Utility of Weinreb's Amide"; Journal fur Praktische Chemie; 342; 2000; 340-347.
Spiegel et al; "Nature Reviews Immunology"; vol. 11, No. 6; pp. 403-415; Jun. 2011.
Srivastava et al; "Synthesis of 3-Aryl-5-[Thien-3-YL Methyl]-1,2,4-Oxadiazoles", Synthetic Communications, 1999, pp. 1437-1450, vol. 29.
Stauffer S. et al., Organic Letters, vol. 2, No. 10, pp. 1423-1426 (2000).
Suzuki et al; "Synthesis of the Selective 5-Hydroxytryptamine 4 (5-HT4) Receptor Agonist (+)-(S)-2-Chloro-5-methoxy-4-[5-(2-plperydylmethyl)-1,2,4-oxadiazol-3-yl]aniline"; Chem. Pharm. Bull.; 1999, pp. 120-122, vol. 47.
Szczepankiewicz et al; "Aminopyridine-based c-Jun N-Terminal Kinase Inhibitors with Cellular Activity and Minimal Cross-Kinase Activity"; J. Med. Chem., vol. 49, pp. 3563-3580; (2006).
Trapani et al; "Propofol Analgoues. Synthesis, Relationships between Structure and Affinity at GABAA Receptor in Rat Brain, and Differential Electrophysiological Profile at Recombinant Human GABAA Receptors"; Journal of Medicinal Chemistry, 1998, pp. 1846-1854, vol. 41.
Tsukerman et al; "Basicity and Structure of .alpha., .beta.-unsaturated Ketones of a Heterocyclic Series. VII. Methyl-substituted Analogs of Chalcones"; Chemical Abstracts Service; XP002467039; STN Databse Accession No.; 1971: 87024.
Van Der Giet et al; "Relevance and Potential, Etc."; Biol. Chem.; 389, pp. 1381-1390; (2008).
Vermonden et al; "Synthesis of 4-functionalized terdendate pyridine-based ligands"; Tetrahedron, vol. 59, pp. 5039-5045; (2003).
Wagaw S. et al., J. Org. Chem., vol. 61, pp. 7240-7241 (1996).
Wild et al; "Asymmetric Synthesis of (S)-(—)-acromelobic Acid"; Eur. J. Org. Chem.; 2003; pp. 4445-4449.
Wolfe J. P. et al., J. Org. Chem. vol. 65, pp. 1158-1174 (2000).

Xu et al; "Acyclic Analogues of Adenosine Biphosphates as P2Y Receptor Antagonists: Phosphate Substitution Leads to Multiple Pathways of Inhibition of Platelet Aggregation"; Journal of Medicinal Chemistry, 2002, pp. 5694-5709, vol. 45.
Yan et al, "Discovery of 3-arylpropionic Acids as Potent Agonists of Spingosine-1-phosphate Receptor-1 (S1P1) with High Selectivity Against All Other Known S1P Receptor Subtypes"; Bioorganic and Medicinal Chemistry Letters, 2006, pp. 3679-3683, vol. 16, No. 14.
Zhen et al, "Discovery of Potent 3,5-Diphenyl-1,2,4-oxadiazole Sphingosine-1-phosphate-1 (S1P1) Receptor Agonists with Exceptional Selectivity Against S1P2 and S1P", Journal of Medicinal Chemistry, 2005, pp. 6169-6173, vol. 48, No. 20.
Ziener, U. et al., Chemistry—A European Journal, vol. 6, pp. 41332-4139 (2000).
Brain, C.T., et al., Tetrahedron Letters, vol. 40, pp. 3275-3278, (1999).
Buzard, et al., Expert Opinion on Therapeutic Patents, vol. 18, No. 10, pp. 1141-1159, (2008).
Chakraborti, A.K., et al., Tetrahedron, vol. 55, pp. 13265-13268, (1999).
Doucet, H., Eur. J. Org. Chem. pp. 2013-2030, (2008).
Furstner, A., Angew. Chem., vol. 114, pp. 632-635, (2002).
Furstner, A., et al., J. Am. Chem. Soc. vol. 124, pp. 13856-13863, (2002).
Gangloff, A.R., et al, Tetrahedron Letters, vol. 42, pp. 1441-1443, (2001).
Garcia, M.A., et al., J. Med. Chem., vol. 48, pp. 4068-4075, (2005).
Gould, P.L., "Salt Selection for Basic Drugs", International Journal of Pharmaceutics, vol. 33, pp. 201-217, (1986).
Greene, T.W., et al., Protective Groups in Organic Synthesis, $3^{rd}$ Edition, Wiley New York, (1999).
Hamze, J. F., et al., J. Org. Chem., vol. 68, pp. 7316-7321, (2003).
Hla, T., et al., J. Biol. Chem., vol. 265, pp. 9308-9313, (1990).
John, E.O., et al., Inorganic Chemistry, vol. 27, pp. 3100-3104, (1988).
Kaboudin, K., et al. Heterocycles, vol. 60, pp. 2287-2292, (2003).
Kerins, F., et al., J. Org. Chem., vol. 67, pp. 4968-4971, (2002).
Kocienski, P. J., Protecting Groups, Thieme Stuttgart, (1994).
Matsushita, H., et al., J. Org. Chem., vol. 47, pp. 4161-4165, (1982).
Meyer, E., et aol, Synthesis, pp. 899-905 (2003).
Poulain, R.F., et al., Tetrahedron Letters, vol. 42, pp. 1495-1498, (2001).
Remington, The Science and Practice of Pharmacy, $21^{st}$ Edition, Part 5, "Pharmaceutical Manufacturing", (2005).
Roth, B., et al., J. Med. Chem. vol. 31, pp. 122-129, (1988).
Schurer, et al., ACS Chemical Biolog, vol. 3, No. 8, pp. 486-498, (2008).
Srivastava, R.M., et al., Synthetic Commun., vol. 29, pp. 1437-1450, (1999).
Suzuki, T, et al., Chem. Pharm. Bull., vol. 47, pp. 120-122, (1999).
Trapani, G. , et al., J. Med. Chem., vol. 41, pp. 1846-1854, (1998).
Wild, N., et al., Eur. J. Org. Chem., pp. 4445-4449, (2003).
Yan, et al., Bioorg. & Med. Chem. Lett., vol. 16, pp. 3679-3683, (2006).
U.S. Appl. No. 13/980,764, filed Jan. 18, 2012, Bolli et al.
Notice of Allowance dated Jun. 19, 2013 for U.S. Appl. No. 12/310,801.
Notice of Allowance dated Jul. 17, 2013 for U.S. Appl. No. 12/531,374.
Notice of Allowance dated Jun. 24, 2013 for U.S. Appl. No. 12/920,656.

* cited by examiner

PYRIDIN-4-YL DERIVATIVES

CROSS REFERENCE TO RELATED APPLICATIONS

This application is a United States Application under 35 USC §371 claiming benefit of PCT/IB2010/053224, filed Jul. 15, 2010, which claims priority to PCT/IB2009/053089, filed Jul. 16, 2009, the contents of each of which are incorporated herein by reference.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory diseases.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory diseases and to improve vascular functionality. Prior art document WO 2008/029371 discloses compounds that act as S1P1/EDG1 receptor agonists and show an immunomodulating effect as described above. Unexpectedly, it has been found that the compounds of the present invention have a reduced potential to constrict airway tissue/vessels when compared to compounds of the prior art document WO 2008/029371. The compounds of the present invention therefore demonstrate superiority with respect to their safety profile, e.g. a lower risk of bronchoconstriction.

Examples of WO 2008/029371, which are considered closest prior art analogues are shown in FIG. 1.

FIG. 1: Structure of Examples of prior art document WO 2008/029371, which are considered closest analogues to the compounds of the present invention.

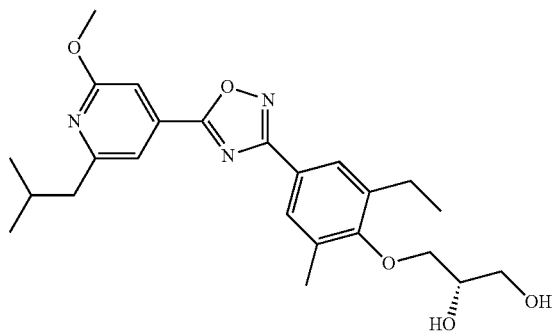

Example 222

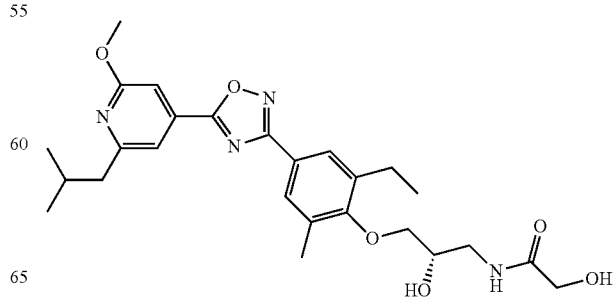

Example 226

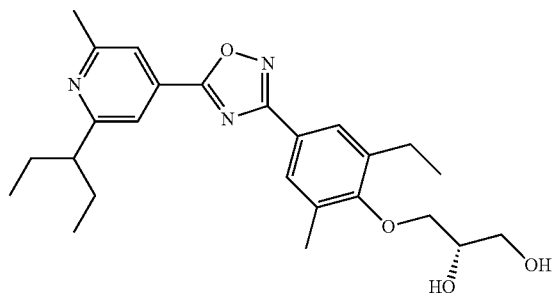

Example 196

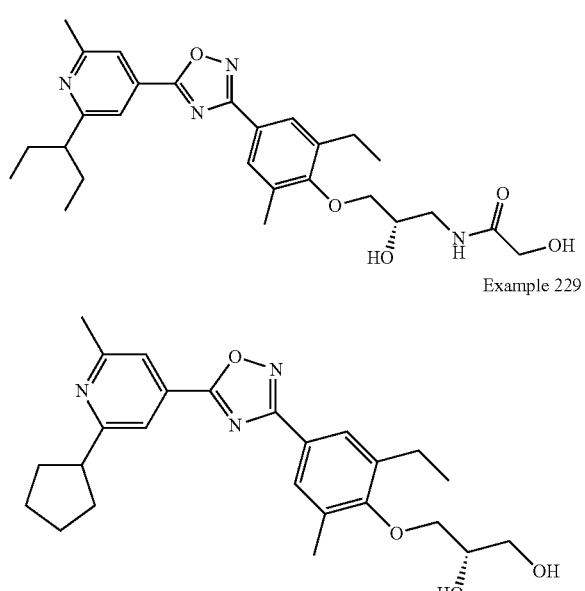

Example 204

Example 229

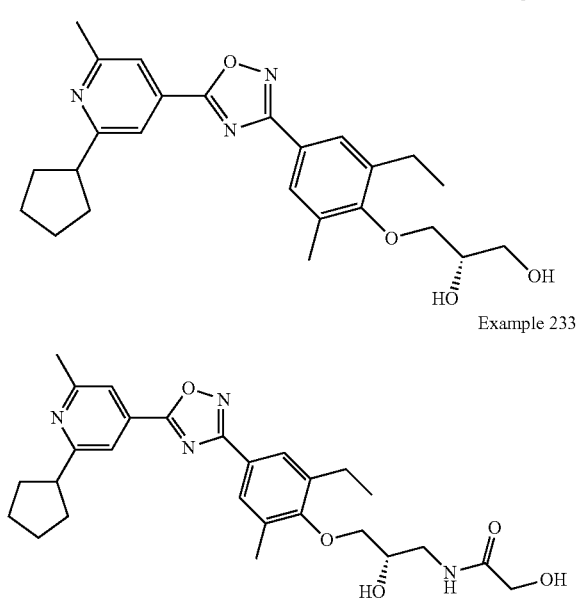

Example 233

The data on the constriction of rat trachea rings compiled in Table 1 illustrate the superiority of the compounds of the present invention as compared to compounds of prior art document WO 2008/029371.

For instance, the compounds of Example 1 and 6 of the present invention show a significantly reduced potential to constrict rat trachea rings when compared to the compounds of prior art Examples 222 and 226 of WO 2008/029371, respectively. Furthermore, the compounds of Example 1 and 6 of the present invention also show a reduced potential to constrict rat trachea rings when compared to the compounds of prior art Examples 196 and 204 of WO 2008/029371, respectively. These data demonstrate that compounds wherein $R^1$ represents 3-pentyl and $R^2$ represents methoxy are superior compared to the closest prior art compounds of WO 2008/029371, i.e. the compounds wherein $R^1$ represents an isobutyl and $R^2$ represents methoxy or wherein $R^1$ represents methyl and $R^2$ represents 3-pentyl. Moreover, also the compound of Example 16 of the present invention, wherein $R^1$ is 3-methyl-but-1-yl and $R^2$ is methoxy, exhibits a markedly reduced potential to constrict rat trachea rings when compared to its closest analogue prior art Example 226 of WO 2008/029371 wherein $R^1$ is isobutyl and $R^2$ is methoxy.

The unexpected superiority of the compounds of the present invention is also evident from the observation that the compounds of Example 2 and 7 of the present invention show a markedly reduced potential to constrict rat trachea rings when compared to the compounds of prior art Examples 229 and 233 of WO 2008/029371, respectively. This proves that compounds wherein $R^1$ represents cyclopentyl and $R^2$ represents methoxy are superior compared to the closest prior art compounds of WO 2008/029371, i.e. the compounds wherein $R^1$ represents methyl and $R^2$ represents cyclopentyl.

Also, the compound of Example 3 of the present invention exhibits the same low potential to constrict rat trachea rings as its S-enantiomer, i.e. the compound of Example 2 of the present invention, indicating that the configuration at this position has no significant effect on trachea constriction. Furthermore, also Example 21 of the present invention exhibits the same low potential to constrict rat trachea rings as present Example 2, which differs from Example 21 only by the linker A (forming a 5-pyridin-4-yl-[1,2,4]oxadiazole instead of a 3-pyridin-4-yl-[1,2,4]oxadiazole). This indicates that also the nature of the oxadiazole is not critical regarding trachea constriction.

TABLE 1

Rat trachea constriction in % of the constriction induced by 50 mM KCl. n.d. = not determined. For experimental details and further data see Example 33.

| | % trachea constriction | |
|---|---|---|
| Compound | at 1 µM | at 10 µM |
| Prior art Example 196 | 82 | n.d. |
| Prior art Example 204 | 112 | n.d. |
| Prior art Example 222 | <5 | 124 |
| Prior art Example 226 | 133 | n.d. |
| Prior art Example 229 | 18 | n.d. |
| Prior art Example 233 | 120* | n.d. |
| Example 1 | <5 | 24 |
| Example 2 | <5 | <5 |
| Example 3 | <5 | n.d. |
| Example 6 | <5 | 100 |
| Example 7 | 50 | n.d. |
| Example 16 | <5 | n.d. |
| Example 21 | <5 | n.d. |

*result obtained at a compound concentration of 300 nM.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T., *J. Biol Chem.* 265

(1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in experimental part).

i) In a first embodiment, the invention relates to pyridine compounds of the Formula (I),

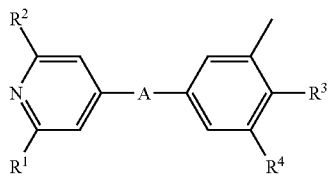

Formula (I)

wherein
A represents

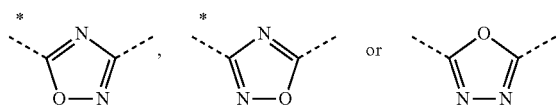

wherein the asterisks indicate the bond that is linked to the pyridine group of Formula (I);
R¹ represents 3-pentyl, 3-methyl-but-1-yl, cyclopentyl, or cyclohexyl;
R² represents methoxy;
R³ represents 2,3-dihydroxypropoxy, —OCH₂—CH(OH)—CH₂—NHCO—CH₂OH, —OCH₂—CH(OH)—CH₂N(CH₃)—CO—CH₂OH, —NHSO₂CH₃, or —NHSO₂CH₂CH₃; and
R⁴ represents ethyl or chloro.

ii) Another embodiment of the invention relates to pyridine derivatives according to embodiment i), wherein the stereocenter of the R³ groups 2,3-dihydroxypropoxy, —OCH₂—CH(OH)—CH₂—NHCO—CH₂OH, and —OCH₂—CH(OH)—CH₂N(CH₃)—CO—CH(OH is in the S-configuration.

iii) Another embodiment of the invention relates to pyridine derivatives according to embodiment i), wherein the stereocenter of the R³ groups 2,3-dihydroxypropoxy, —OCH₂—CH(OH)—CH₂—NHCO—CH₂OH, and —OCH₂—CH(OH)—CH₂N(CH₃)—CO—CH(OH is in the R-configuration.

iv) Another embodiment of the invention relates to pyridine derivatives according to any one of the embodiments i) to iii), wherein A represents

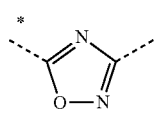

wherein the asterisk indicates the bond that is linked to the pyridine group of Formula (I).
v) Another embodiment of the invention relates to pyridine derivatives according to any one of the embodiments i) to iii), wherein A represents

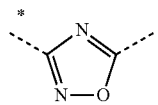

wherein the asterisk indicates the bond that is linked to the pyridine group of Formula (I).
vi) Another embodiment of the invention relates to pyridine derivatives according to any one of the embodiments i) to iii), wherein A represents

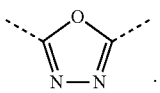

vii) Another embodiment of the invention relates to pyridine derivatives according to any one of the embodiments i) to vi), wherein R¹ represents 3-pentyl.
viii) Another embodiment of the invention relates to pyridine derivatives according to any one of the embodiments i) to vi), wherein R¹ represents 3-methyl-but-1-yl.
ix) Another embodiment of the invention relates to pyridine derivatives according to any one of the embodiments i) to vi), wherein R¹ represents cyclopentyl.
x) Another embodiment of the invention relates to pyridine derivatives according to any one of the embodiments i) to vi), wherein R¹ represents cyclohexyl.
xi) Another embodiment of the invention relates to pyridine derivatives according to any one of the embodiments i) to x), wherein R³ represents 2,3-dihydroxypropoxy.
xii) Another embodiment of the invention relates to pyridine derivatives according to any one of the embodiments i) to x), wherein R³ represents —OCH₂—CH(OH)—CH₂—NHCO—CH(OH.
xiii) Another embodiment of the invention relates to pyridine derivatives according to any one of the embodiments i) to x), wherein R³ represents —OCH₂—CH(OH)—CH₂N(CH₃)—CO—CH₂OH.
xiv) Another embodiment of the invention relates to pyridine derivatives according to any one of the embodiments i) to x), wherein R³ represents —NHSO₂CH₃.
xv) Another embodiment of the invention relates to pyridine derivatives according to any one of the embodiments i) to x), wherein R³ represents —NHSO₂CH₂CH₃.
xvi) Another embodiment of the invention relates to pyridine derivatives according to any one of the embodiments i) to xv), wherein R⁴ represents ethyl.
xvii) Another embodiment of the invention relates to pyridine derivatives according to any one of the embodiments i) to xv), wherein R⁴ represents chloro.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term "pharmaceutically acceptable salts" refers to non-toxic, inorganic or organic acid and/or base addition salts. Reference can be made to "Salt selection for basic drugs", Int. J. Pharm. (1986), 33, 201-217.

The present invention also includes isotopically labelled, especially $^2$H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Examples of pyridine compounds according to Formula (I) are selected from:
(S)-3-(2-Ethyl-4-{5-[2-(1-ethyl-propyl)-6-methoxy-pyridin-4-yl]-[1,2,4]oxadiazol-3-yl}-6-methyl-phenoxy)-propane-1,2-diol;
(S)-3-{4-[5-(2-cyclopentyl-6-methoxy-pyridin-4-yl)-[1,2,4]oxadiazol-3-yl]-2-ethyl-6-methyl-phenoxy}-propane-1,2-diol;
(R)-3-{4-[5-(2-cyclopentyl-6-methoxy-pyridin-4-yl)-[1,2,4]oxadiazol-3-yl]-2-ethyl-6-methyl-phenoxy}-propane-1,2-diol;
(S)-3-{4-[5-(2-cyclohexyl-6-methoxy-pyridin-4-yl)-[1,2,4]oxadiazol-3-yl]-2-ethyl-6-methyl-phenoxy}-propane-1,2-diol;
ethanesulfonic acid {2-chloro-4-[5-(2-cyclopentyl-6-methoxy-pyridin-4-yl)-[1,2,4]oxadiazol-3-yl]-6-methyl-phenyl}-amide;
N—[(S)-3-(2-ethyl-4-{5-[2-(1-ethyl-propyl)-6-methoxy-pyridin-4-yl]-[1,2,4]oxadiazol-3-yl}-6-methyl-phenoxy)-2-hydroxy-propyl]-2-hydroxy-acetamide;
N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-acetamide;
N—((S)-3-{4-[5-(2-cyclohexyl-6-methoxy-pyridin-4-yl)-[1,2,4]oxadiazol-3-yl]-2-ethyl-6-methyl-phenoxy}-2-hydroxy-propyl)-2-hydroxy-acetamide;
N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide;
N-(2-chloro-4-{5-[2-(1-ethyl-propyl)-6-methoxy-pyridin-4-yl]-[1,2,4]oxadiazol-3-yl}-6-methyl-phenyl)-methanesulfonamide;
N-{2-chloro-4-[5-(2-cyclopentyl-6-methoxy-pyridin-4-yl)-[1,2,4]oxadiazol-3-yl]-6-methyl-phenyl}-methanesulfonamide;
(S)-3-{2-chloro-4-[5-(2-cyclopentyl-6-methoxy-pyridin-4-yl)-[1,2,4]oxadiazol-3-yl]-6-methyl-phenoxy}-propane-1,2-diol;
N—((S)-3-{2-chloro-4-[5-(2-cyclopentyl-6-methoxy-pyridin-4-yl)-[1,2,4]oxadiazol-3-yl]-6-methyl-phenoxy}-2-hydroxy-propyl)-2-hydroxy-acetamide;

(S)-3-(2-ethyl-4-{5-[2-methoxy-6-(3-methyl-butyl)-pyridin-4-yl]-[1,2,4]oxadiazol-3-yl}-6-methyl-phenoxy)-propane-1,2-diol;
N—[(S)-3-(2-ethyl-4-{5-[2-methoxy-6-(3-methyl-butyl)-pyridin-4-yl]-[1,2,4]oxadiazol-3-yl}-6-methyl-phenoxy)-2-hydroxy-propyl]-2-hydroxy-acetamide;
N-{2-chloro-4-[5-(2-cyclohexyl-6-methoxy-pyridin-4-yl)-[1,2,4]oxadiazol-3-yl]-6-methyl-phenyl}-methanesulfonamide;
N-(2-ethyl-4-{5-[2-(1-ethyl-propyl)-6-methoxy-pyridin-4-yl]-[1,2,4]oxadiazol-3-yl]-6-methyl-phenyl}-methanesulfonamide;
N-{4-[5-(2-cyclopentyl-6-methoxy-pyridin-4-yl)-[1,2,4]oxadiazol-3-yl]-2-ethyl-6-methyl-phenyl}-methanesulfonamide;
N-{4-[5-(2-cyclohexyl-6-methoxy-pyridin-4-yl)-[1,2,4]oxadiazol-3-yl]-2-ethyl-6-methyl-phenyl}-methanesulfonamide;
(S)-3-{4-[3-(2-cyclopentyl-6-methoxy-pyridin-4-yl)-[1,2,4]oxadiazol-5-yl]-2-ethyl-6-methyl-phenoxy}-propane-1,2-diol;
(R)-3-{4-[3-(2-cyclopentyl-6-methoxy-pyridin-4-yl)-[1,2,4]oxadiazol-5-yl]-2-ethyl-6-methyl-phenoxy}-propane-1,2-diol;
N—((S)-3-{4-[3-(2-cyclopentyl-6-methoxy-pyridin-4-yl)-[1,2,4]oxadiazol-5-yl]-2-ethyl-6-methyl-phenoxy}-2-hydroxy-propyl)-2-hydroxy-acetamide;
N—((R)-3-{4-[3-(2-cyclopentyl-6-methoxy-pyridin-4-yl)-[1,2,4]oxadiazol-5-yl]-2-ethyl-6-methyl-phenoxy}-2-hydroxy-propyl)-2-hydroxy-acetamide;
(S)-3-{4-[5-(2-cyclopentyl-6-methoxy-pyridin-4-yl)-[1,3,4]oxadiazol-2-yl]-2-ethyl-6-methyl-phenoxy}-propane-1,2-diol;
(R)-3-{4-[5-(2-cyclopentyl-6-methoxy-pyridin-4-yl)-[1,3,4]oxadiazol-2-yl]-2-ethyl-6-methyl-phenoxy}-propane-1,2-diol;
N—((S)-3-{4-[5-(2-cyclopentyl-6-methoxy-pyridin-4-yl)-[1,3,4]oxadiazol-2-yl]-2-ethyl-6-methyl-phenoxy}-2-hydroxy-propyl)-2-hydroxy-acetamide; and
N—((R)-3-{4-[5-(2-cyclopentyl-6-methoxy-pyridin-4-yl)-[1,3,4]oxadiazol-2-yl]-2-ethyl-6-methyl-phenoxy}-2-hydroxy-propyl)-2-hydroxy-acetamide.

Examples of pyridine compounds according to Formula (I) are further also selected from:
(S)-3-{2-chloro-4-[5-(2-cyclohexyl-6-methoxy-pyridin-4-yl)-[1,2,4]oxadiazol-3-yl]-6-methyl-phenoxy}-propane-1,2-diol; and
N-(2-ethyl-4-(5-(2-isopentyl-6-methoxypyridin-4-yl)-1,2,4-oxadiazol-3-yl)-6-methylphenyl)methanesulfonamide.

The compounds of Formula (I) and their pharmaceutically acceptable salts can be used as medicaments, e.g. in the form of pharmaceutical compositions for enteral or parenteral administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders associated with an activated immune system and to be prevented/treated with the compounds of Formula (I) are for example selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; aneryth-roplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of Formula (I) are selected from multiple sclerosis and psoriasis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

Compounds of Formula (I) which represent a 5-pyridin-4-yl-[1,2,4]oxadiazole derivative, are prepared by reacting a compound of Structure 1 in a solvent such as toluene, pyridine, DMF, THF, dioxane, DME, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, $NEt_3$, etc.), tetraalkylammonium salts, or water removing agents (e.g. oxalyl chloride, a carboxylic acid anhydride, $POCl_3$, $PCl_5$, $P_4O_{10}$, molecular sieves, Burgess reagent, etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

Structure 1

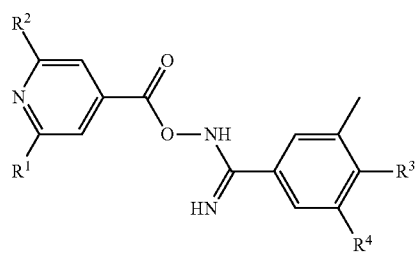

Compounds of Structure 1 may be prepared by reacting a compound of Structure 2 with a compound of Structure 3 in a solvent such as DMF, THF, DCM, etc. in the presence of one or more coupling agents such as TBTU, DCC, EDC, HBTU, CDI, etc. and in the presence or absence of a base such as $NEt_3$, DIPEA, NaH, $K_2CO_3$, etc. (Lit.: e.g. A. Hamze, J.-F. Hernandez, P. Fulcrand, J. Martinez, *J. Org. Chem.* 68 (2003) 7316-7321; and the literature cited above).

Structure 2

Structure 3

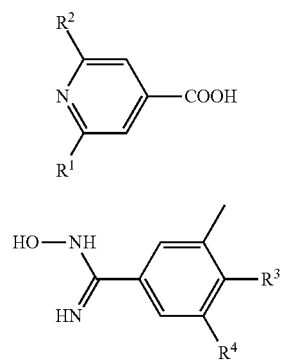

Compounds of Formula (I) which represent a 3-pyridin-4-yl-[1,2,4]oxadiazole derivative, are prepared in an analogous fashion (Lit.: e.g. C. T. Brain, J. M. Paul, Y. Loong, P. J. Oakley, *Tetrahedron Lett.* 40 (1999) 3275-3278) by reacting a compound of Structure 4 with a compound of Structure 5 and subsequent cyclisation of the corresponding hydroxyamidine ester intermediate.

Structure 4

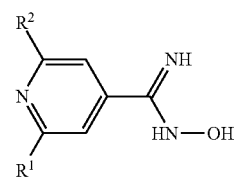

Structure 5

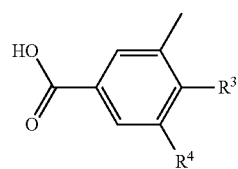

Compounds of Structure 3 and 4 may be prepared by reacting a compound of Structure 6 and 7, respectively, with hydroxylamine or one of its salts in a solvent such as MeOH, EtOH, pyridine, etc. in the presence or absence of a base such as $Na_2CO_3$, $K_2CO_3$, potassium tert.butylate, $NEt_3$, etc. (Lit.: e.g. E. Meyer, A. C. Joussef, H. Gallardo, *Synthesis* 2003, 899-905, WO 2004/035538 (Merck & Co., Inc., USA)).

Structure 6

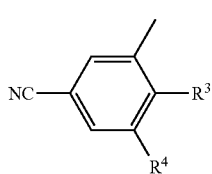

Structure 7

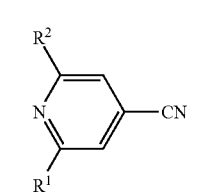

Depending on the nature of the functionalities present in residue $R^3$ in Structures 3, 5 and 6, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, $3^{rd}$ Edition, Wiley New York, 1991; P. J. Kocienski, Protecting Groups, Thieme Stuttgart, 1994). Alternatively, the desired residues $R^3$ and $R^4$, in particular $R^3$, may also be introduced in later steps that follow the coupling of the pyridine compounds of Structure 2 or 4 with the phenyl derivatives of Structure 3 or 5 by using a suitable precursor of a compound of Structure 3 and 5. The phenyl compounds of Structure 3, 5 and 6 or their precursors are either commercially available or are prepared according to procedures known to a person skilled in the art.

Structure 8

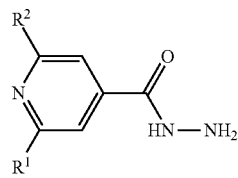

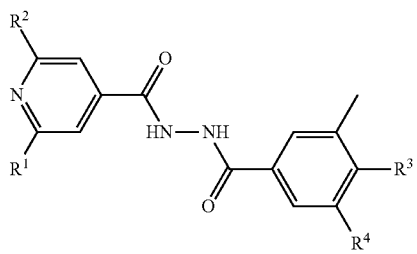

Structure 9

Compounds of Formula (I) which represent a 2-pyridin-4-yl-[1,3,4]oxadiazole are prepared similarly by reacting a compound of Structure 2 with hydrazine (by using a coupling reagent such as TBTU, DCC, EDC, HBTU, PyBOP, CDI, etc.) to form a compound of Structure 8 which is then coupled with a compound of Structure 5 to give a compound of Structure 9. A compound of Structure 9 can also be prepared by following the reverse reaction order i.e. by first coupling a compound of Structure 5 with hydrazine followed by reacting the corresponding hydrazide intermediate with a compound of Structure 2. Dehydration of a compound of Structure 9 to form the desired 2-pyridin-4-yl-[1,3,4]oxadiazole derivative is affected by treating a compound of Structure 9 with a reagent such as $POCl_3$, $CCl_4$ or $CBr_4$ in combination with $PPh_3$, $P_2O_5$, Burgess reagent, etc. in a solvent such as toluene, MeCN, dioxane, THF, $CHCl_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y. Loong, P. J. Oakley, *Tetrahedron Lett.* 40 (1999) 3275-3278).

Methods that effect the transformation of a compound of Structure 2 or 5 into a compound of Structure 7 or 6, respectively, or the opposite, are known to a person skilled in the art.

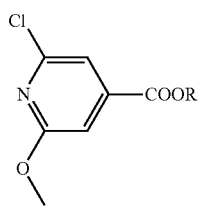

Structure 10

Compounds of Structure 2 may be prepared by reacting 2,6-dichloro-isonicotinic acid or a suitable ester derivative thereof with methanol in the presence or absence of a base such as NaOH, NaOMe, potassium tert. butoxide, etc. in a solvent such as methanol, THF, dioxane etc. to give a compound of Structure 10 (R=H or preferably Me, Et, tert.-butyl, etc.) (Lit.: e.g. N. Wild, U. Groth, *Eur. J. Org. Chem.* 2003, 4445-4449). The compound of Structure 10 may then be reacted with the appropriate alkyl or cycloalkyl Zn reagent under Negishi conditions (Lit.: e.g. H. Matsushita, E. Negishi, *J. Org. Chem.* 47 (1982) 4161-4165), with an appropriate alkyl or cycloalkyl Grignard reagent for instance in the presence of $Fe(acac)_3$ in a solvent such as THF, dioxane, DMF, NMP, etc., or combinations thereof, at temperatures ranging from −78 to 25° C. under Fürstner conditions (Lit.: e.g. A. Fürstner, A. Leitner, M. Mendez, H. Krause, *J. Am. Chem. Soc.* 124 (2002) 13856-13863; A. Fürstner, A. Leitner, *Angew. Chem.* 114 (2002) 632-635) or with an appropriate alkyl, cycloalkyl or alkenyl boron derivative (Lit.: e.g. F. Kerins, D. F. O'Shea, *J. Org. Chem.* 67 (2002) 4968-4971) under Suzuki coupling conditions (Lit.: e.g. H. Doucet, *Eur. J. Org. Chem.* 2008, 2013-2030). In case alkenyl boron derivatives are used to introduce the carbon framework of $R^1$, a subsequent hydrogenation step is required to establish the desired alkyl or cycloalkyl group. Finally, in case a pyridine-4-carboxylic acid ester has been employed in the steps described above, ester hydrolysis under basic or acid reaction conditions furnishes the desired compound of Structure 2.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as $NEt_3$, diethylamine) and eluent B (hexane), at a flow rate of 0.8 to 150 mL/min.

Experimental Part

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% MeCN in water, 1 min, with 0.04% trifluoroacetic acid, flow: 4.5 mL/min), $t_R$ is given in min, (retention times or LC-MS marked with ** refer to an LC run under the following conditions: column: Zorbax Extended C18, 1.8 μM, 4.6× 20 mm, gradient: 5-95% MeCN in water, 1 min, with 0.04% TFA, flow: 4.5 mL/min); by TLC (TLC-plates from Merck, Silica gel 60 $F_{254}$); or by melting point. Compounds are purified by preparative HPLC (column: X-terra RP18, 50×19 mm, 5 μm, gradient: 10-95% MeCN in water containing 0.5% of formic acid) or by MPLC (Labomatic MD-80-100 pump, Linear UVIS-201 detector, column: 350×18 mm, Labogel-RP-18-5s-100, gradient: 10% MeOH in water to 100% MeOH).

| Abbreviations (as used herein): | |
|---|---|
| aq. | aqueous |
| BSA | bovine serum albumin |
| Burgess reagent | methoxycarbonylsulfamoyl triethylammonium hydroxide |
| CC | column chromatography |
| CDI | carbonyl diimidazole |
| DCC | N,N'-dicyclohexyl carbodiimide |
| DCM | dichloromethane |
| DEAD | diethyl-diazodicarboxylate |
| DIPEA | Hüning's base, diethylisopropylamine |
| DME | 1,2-dimethoxyethane |
| DMF | dimethylformamide |
| DMSO | dimethylsulfoxide |
| dppf | 1,1'-bis(diphenylphosphino)ferrocene |
| EA | ethyl acetate |
| EDC | N-(3-dimethylaminopropyl)-N'-ethyl-carbodiimide |
| Et | ethyl |
| EtOH | ethanol |

-continued

| Abbreviations (as used herein): | |
|---|---|
| Fe(acac)₃ | iron(III) acetylacetone-complex |
| h | hour(s) |
| HBTU | O-(benzotriazol-1-yl)-N,N,N',N'-tetramethyluronium hexafluorophosphate |
| HOBt | 1-hydroxy-benzotriazole |
| HPLC | high performance liquid chromatography |
| HV | high vacuum conditions |
| LC-MS | liquid chromatography - mass spectrometry |
| Lit. | literature |
| Me | methyl |
| MeCN | acetonitrile |
| MeOH | methanol |
| min | minute(s) |
| MPLC | medium pressure liquid chromatography |
| NaOAc | sodium acetate |
| NEt₃ | triethylamine |
| NMP | 1-methyl-2-pyrrolidone |
| org. | organic |
| PPh₃ | triphenylphosphine |
| PyBOP | benzotriazol-1-yl-oxy-tris-pyrrolidino-phosphonium-hexafluoro-phosphate |
| prep. | preparative |
| rt | room temperature |
| sat. | saturated |
| S1P | sphingosine 1-phosphate |
| TBME | tert.-butyl methyl ether |
| TBTU | 2-(1H-benzotriazole-1-yl)-1,2,3,3-tetramethyluronium tetrafluoroborate |
| tert. | tertiary |
| TFA | trifluoroacetic acid |
| THF | tetrahydrofuran |
| TLC | thin layer chromatography |
| $t_R$ | retention time |

Preparation of Intermediates

2-Chloro-6-methyl-isonicotinic acid

The title compound and its ethyl ester are commercially available.

2-(1-Ethyl-propyl)-6-methoxy-isonicotinic acid a) To a solution of 2,6-dichloroisonicotinic acid (200 g, 1.04 mol) in methanol (3 L), 32% aq. NaOH (770 mL) is added. The stirred mixture becomes warm (34° C.) and is then heated to 70° C. for 4 h before it is cooled to rt. The mixture is neutralised by adding 32% aq. HCl (100 mL) and 25% aq. HCl (700 mL). The mixture is stirred at rt overnight. The white precipitate that forms is collected, washed with methanol and dried. The filtrate is evaporated and the residue is suspended in water (200 mL). The resulting mixture is heated to 60° C. Solid material is collected, washed with water and dried. The combined crops give 2-chloro-6-methoxy-isonicotinic acid (183 g) as a white solid; LC-MS: $t_R$=0.80 min, [M+1]⁺=187.93.

b) To a suspension of 2-chloro-6-methoxy-isonicotinic acid (244 g, 1.30 mol) in methanol (2.5 L), $H_2SO_4$ (20 mL) is added. The mixture is stirred at reflux for 24 h before it is cooled to 0° C. The solid material is collected, washed with methanol (200 mL) and water (500 mL) and dried under HV to give 2-chloro-6-methoxy-isonicotinic acid methyl ester (165 g) as a white solid; LC-MS: $t_R$=0.94 min, [M+1]⁺=201.89.

c) Under argon, Pd(dppf) (3.04 g, 4 mmol) is added to a solution of 2-chloro-6-methoxy-isonicotinic acid methyl ester (50 g, 0.248 mol) in THF (100 mL). A 0.5 M solution of 3-pentylzincbromide in THF (550 mL) is added via dropping funnel. Upon complete addition, the mixture is heated to 85° C. for 18 h before it is cooled to rt. Water (5 mL) is added and the mixture is concentrated. The crude product is purified by filtration over silica gel (350 g) using heptane:EA 7:3 to give 2-(1-ethyl-propyl)-6-methoxy-isonicotinic acid methyl ester (53 g) as a pale yellow oil; ¹H NMR (CDCl₃): δ0.79 (t, J=7.5 Hz, 6H), 1.63-1.81 (m, 4H), 2.47-2.56 (m, 1H), 3.94 (s, 3H), 3.96 (s, 3H), 7.12 (d, J=1.0 Hz, 1H), 7.23 (d, J=1.0 Hz, 1H).

d) A solution of 2-(1-ethyl-propyl)-6-methoxy-isonicotinic acid methyl ester (50 g, 0.211 mol) in ethanol (250 mL), water (50 mL) and 32% aq. NaOH (50 mL) is stirred at 80° C. for 1 h. The mixture is concentrated and the residue is dissolved in water (200 mL) and extracted with TBME. The org. phase is separated and washed once with water (200 mL). The TBME phase is discarded. The combined aq. phases are acidified by adding 25% aq. HCl and then extracted with EA (400+200 mL). The combined org. extracts are concentrated. Water (550 mL) is added to the remaining residue. The mixture is heated to 70° C., cooled to rt and the precipitate that forms is collected and dried to give the title compound (40.2 g) as a white solid; LC-MS: $t_R$=0.95 min, [M+1]⁺=224.04; ¹H NMR (D₆-DMSO): δ 0.73 (t, J=7.3 Hz, 6H), 1.59-1.72 (m, 4H), 2.52-2.58 (m, 1H), 3.88 (s, 3H), 7.00 (d, J=1.0 Hz, 1H), 7.20 (d, J=1.0 Hz, 1H).

2-Methoxy-6-(3-methyl-butyl)-isonicotinic acid

The title compound is prepared in analogy to 2-(1-ethyl-propyl)-6-methoxy-isonicotinic acid; LC-MS: $t_R$=0.94 min, [M+1]⁺=224.05; ¹H NMR (D₆-DMSO): δ 0.92 (d, J=5.8 Hz, 6H), 1.54-1.62 (m, 3H), 2.70-2.76 (m, 2H), 3.88 (s, 3H), 6.99 (s, 1H), 7.25 (s, 1H), 13.52 (s).

2-Cyclopentyl-6-methoxy-isonicotinic acid

The title compound is prepared in analogy to 2-(1-ethyl-propyl)-6-methoxy-isonicotinic acid; LC-MS: $t_R$=0.93 min, [M+1]⁺=222.02; ¹H NMR (CDCl₃): δ 1.68-1.77 (m, 2H), 1.81-1.90 (m, 4H), 2.03-2.12 (m, 2H), 3.15-3.25 (m, 1H), 3.99 (s, 3H), 7.18 (d, J=1.0 Hz, 1H), 7.35 (d, J=0.8 Hz, 1H).

2-Cyclohexyl-6-methoxy-isonicotinic acid

The title compound is prepared in analogy to 2-(1-ethyl-propyl)-6-methoxy-isonicotinic acid; LC-MS: $t_R$=0.98 min, [M+1]⁺=236.01; ¹H NMR (D₆-DMSO): δ 1.17-1.29 (m, 1H), 1.31-1.43 (m, 2H), 1.44-1.55 (m, 2H), 1.67-1.73 (m, 1H), 1.76-1.83 (m, 2H), 1.84-1.92 (m, 2H), 2.66 (tt, J=11.3, 3.3 Hz, 1H), 3.88 (s, 3H), 7.00 (d, J=1.0 Hz, 1H), 7.23 (d, J=1.0 Hz, 1H).

2-Cyclopentyl-N-hydroxy-6-methoxy-isonicotinamidine a) A solution of 2-cyclopentyl-6-methoxy-isonicotinic acid methyl ester (3.19 g, 13.6 mmol) in 7 N NH₃ in methanol (50 mL) is stirred at 60° C. for 18 h. The solvent is removed in vacuo and the residue is dried under HV to give crude 2-cyclopentyl-6-methoxy-isonicotinamide (3.35 g) as a pale yellow solid; LC-MS**: $t_R$=0.57 min, [M+1]⁺=221.38.

b) Pyridine (8.86 g, 91.3 mmol) is added to a solution of 2-cyclopentyl-6-methoxy-isonicotinamide (3.35 g, 15.2 mmol) in DCM (100 mL). The mixture is cooled to 0° C. before trifluoroacetic acid anhydride (9.58 g, 45.6 mmol) is added portionwise. The mixture is stirred at 0° C. for 1 h before it is diluted with DCM (100 mL) and washed with sat. aq. NaHCO₃ solution (100 mL) and brine (100 mL). The separated org. phase is dried over MgSO₄, filtered and concentrated. The crude product is purified by CC on silica gel eluting with heptane:EA 9:1 to give 2-cyclopentyl-6-methoxy-isonicotinonitrile (2.09 g) as pale yellow oil; LC-MS**: $t_R$=0.80 min, [M+1]$^+$=not detectable; $^1$H NMR (D$_6$-DMSO): δ 1.61-1.82 (m, 6H), 1.94-2.03 (m, 2H), 3.16 (quint, J=7.8 Hz, 1H), 3.89 (s, 3H), 7.15 (s, 1H), 7.28 (s, 1H).

c) To a solution of 2-cyclopentyl-6-methoxy-isonicotinonitrile (2.09 g, 10.3 mmol) in methanol (100 mL), hydroxylamine hydrochloride (2.15 g, 31.0 mmol) and NaHCO$_3$ (3.04 g, 36.2 mmol) are added. The mixture is stirred at 60° C. for 18 h before it is filtered and the filtrate is concentrated. The residue is dissolved in EA (300 mL) and washed with water (30 mL). The washings are extracted back with EA (4×100 mL) and DCM (4×100 mL). The combined org. extracts are dried over MgSO$_4$, filtered, concentrated and dried under HV to give the title compound (2.74 g) as a white solid; LC-MS**: $t_R$=0.47 min, [M+1]$^+$=236.24; $^1$H NMR (D$_6$-DMSO): δ 1.61-1.82 (m, 6H), 1.92-2.01 (m, 2H), 3.04-3.13 (m, 1H), 3.84 (s, 3H), 5.90 (s, 2H), 6.86 (s, 1H), 7.13 (s, 1H), 9.91 (s, 1H).

2-Cyclopentyl-6-methoxy-isonicotinic acid hydrazide a) To a solution of 2-cyclopentyl-6-methoxy-isonicotinic acid (2.00 g, 9.04 mmol), hydrazinecarboxylic acid benzyl ester (1.50 g, 9.04 mmol) and DIPEA (2.34 g, 18.1 mmol) in DCM (40 mL), TBTU (3.19 g, 9.94 mmol) is added. The mixture is stirred at rt for 2 h before it is diluted with EA (250 mL), washed twice with sat. aq. NaHCO$_3$ solution (150 mL) followed by brine (100 mL), dried over MgSO$_4$, filtered and concentrated. The crude product is purified by CC on silica gel eluting with heptane:EA 4:1 to give N'-(2-cyclopentyl-6-methoxy-pyridine-4-carbonyl)-hydrazinecarboxylic acid benzyl ester (2.74 g) as pale yellow oil; LC-MS**: $t_R$=0.74 min, [M+1]$^+$=369.69; $^1$H NMR (D$_6$-DMSO): δ 1.62-1.83 (m, 6H), 1.95-2.05 (m, 2H), 3.10-3.21 (m, 1H), 3.88 (s, 3H), 5.13 (s, 2H), 6.97 (s, 1H), 7.23 (s, 1H), 7.28-7.40 (m, 5H), 9.45 (s, 1H), 10.52 (s, 1H).

b) Pd/C (500 mg, 10% Pd) is added to a solution of N'-(2-cyclopentyl-6-methoxy-pyridine-4-carbonyl)-hydrazinecarboxylic acid benzyl ester (2.74 g, 7.42 mmol) in THF (50 mL) and methanol (50 mL). The mixture is stirred at rt under 1 bar of H$_2$ for 25 h. The catalyst is removed by filtration and the filtrate is concentrated and dried under HV to give the title compound (1.58 g) as an off-white solid; LC-MS**: $t_R$=0.51 min, [M+1]$^+$=236.20; $^1$H NMR (D$_6$-DMSO): δ 1.60-1.82 (m, 6H), 1.94-2.03 (m, 2H), 3.08-3.19 (m, 1H), 3.86 (s, 3H), 4.56 (s br, 2H), 6.93 (d, J=1.0 Hz, 1H), 7.20 (d, J=1.0 Hz, 1H), 9.94 (s, 1H).

3-Ethyl-4-hydroxy-5-methyl-benzonitrile

The title compound is prepared from 3-ethyl-4-hydroxy-5-methyl-benzaldehyde following literature procedures (A. K. Chakraborti, G. Kaur, *Tetrahedron* 55 (1999) 13265-13268); LC-MS: $t_R$=0.90 min; $^1$H NMR (CDCl$_3$): δ1.24 (t, J=7.6 Hz, 3H), 2.26 (s, 3H), 2.63 (q, J=7.6 Hz, 2H), 5.19 (s, 1H), 7.30 (s, 2H).

3-Chloro-4-hydroxy-5-methyl-benzonitrile

The title compound is prepared from commercially available 2-chloro-6-methyl-phenol in analogy to literature procedures (see 3-ethyl-4-hydroxy-5-methyl-benzonitrile); LC-MS: $t_R$=0.85 min. $^1$H NMR (CDCl$_3$): δ2.33 (s, 3H), 6.10 (s, 1H), 7.38 (s, 1H), 7.53 (d, J=1.8 Hz, 1H).

3-Ethyl-4,N-dihydroxy-5-methyl-benzamidine

The title compound is prepared from 3-ethyl-4-hydroxy-5-methyl-benzonitrile or from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

3-Chloro-4,N-dihydroxy-5-methyl-benzamidine

The title compound is prepared from commercially available 2-chloro-6-methyl-phenol in analogy to literature procedures (e.g. B. Roth et al. *J. Med. Chem.* 31 (1988) 122-129; and literature cited for 3-ethyl-4,N-dihydroxy-5-methyl-benzamidine); 3-chloro-4-hydroxy-5-methyl-benzaldehyde: LC-MS: $t_R$=0.49 min, [M+1]$^+$=201.00; $^1$H NMR 82.24 (s, 2H), 2.35 (s, 4H), 5.98 (s br, 1H), 7.59 (d, J=1.8 Hz, 1H), 7.73 (d, J=1.8 Hz, 1H), 9.80 (s, 1H); 3-chloro-4,N-dihydroxy-5-methyl-benzamidine: $^1$H NMR (D$_6$-DMSO): δ 2.21 (s, 3H), 5.72 (s br, 2H), 7.40 (s, 1H), 7.48 (s, 1H), 9.29 (s br, 1H), 9.48 (s br, 1H).

(R)-4-(2,2-Dimethyl-[1,3]dioxolan-4-ylmethoxy)-3-ethyl-N-hydroxy-5-methyl-benzamidine a) To a solution of 3-ethyl-4-hydroxy-5-methyl-benzonitrile (2.89 g, 17.9 mmol) in THF (80 mL), (R)-(2,2-dimethyl-[1,3]dioxolan-4-yl)methanol (2.84 g, 21.5 mmol) followed by triphenylphosphine (5.81 g, 21.5 mmol) is added. The mixture is cooled with an ice-bath before DEAD (9.36 g, 21.5 mmol) is added dropwise. The mixture is stirred at rt for 1 h, the solvent is removed in vacuo and the residue is purified by CC on silica gel eluting with heptane:EA 85:15 to give (R)-4-(2,2-dimethyl-[1,3]dioxolan-4-ylmethoxy)-3-ethyl-5-methyl-benzonitrile (4.45 g) as a pale yellow oil; LC-MS**: $t_R$=0.75 min, [M+1]$^+$=not detected; $^1$H NMR (CDCl$_3$): δ1.25 (t, J=7.5 Hz, 3H), 1.44 (s, 3H), 1.49 (s, 3H), 2.34 (s, 3H), 2.65-2.77 (m, 2H), 3.80-3.90 (m, 2H), 3.94-4.00 (m, 1H), 4.21 (t, J=7.3 Hz, 1H), 4.52 (quint, J=5.8 Hz, 1H), 7.35 (s, 1H), 7.38 (s, 1H).

b) To a mixture of (R)-4-(2,2-dimethyl-[1,3]dioxolan-4-ylmethoxy)-3-ethyl-5-methyl-benzonitrile (4.45 g, 16.2 mmol) and NaHCO$_3$ (4.75 g, 56.6 mmol) in methanol (30 mL), hydroxylamine hydrochloride (3.37 g, 48.5 mmol) is added. The mixture is stirred at 60° C. for 18 h before it is filtered and the solvent of the filtrate is removed in vacuo. The residue is dissolved in EA and washed with a small amount of water and brine. The org. phase is separated, dried over MgSO$_4$, filtered, concentrated and dried to give the title compound (5.38 g) as a white solid; LC-MS**: $t_R$=0.46 min, [M+1]$^+$=309.23; $^1$H NMR (D$_6$-DMSO): δ 1.17 (t, J=7.5 Hz, 3H), 1.33 (s, 3H), 1.38 (s, 3H), 2.25 (s, 3H), 2.57-2.69 (m, 2H), 3.73-3.84 (m, 3H), 4.12 (t, J=7.0 Hz, 1H), 4.39-4.45 (m, 1H), 5.76 (s br, 2H), 7.34 (s, 1H), 7.36 (s, 1H), 9.47 (s, 1H).

(R)-3-Chloro-4-(2,2-dimethyl-[1,3]dioxolan-4-yl-methoxy)-N-hydroxy-5-methyl-benzamidine The title compound is obtained as a colorless oil (1.39 g) in analogy to (R)-4-(2,2-dimethyl-[1,3]dioxolan-4-ylmethoxy)-3-ethyl-N-hydroxy-5-methyl-benzamidine starting from 3-chloro-4-hydroxy-5-methyl-benzonitrile and L-α,β-isopropyliden glycerol; LC-MS: $t_R$=0.66 min, [M+H]$^+$=314.96.

(S)-4-(3-Amino-2-hydroxypropoxy)-3-ethyl-5-methylbenzonitrile a) To a solution of 3-ethyl-4-hydroxy-5-methyl-benzonitrile (5.06 g, 31.4 mmol) in THF (80 mL), PPh$_3$ (9.06 g, 34.5 mmol) and (R)-glycidol (2.29 mL, 34.5 mmol) are added. The mixture is cooled to 0° C. before DEAD in toluene (15.8 mL, 34.5 mmol) is added. The mixture is stirred for 18 h while warming up to rt. The solvent is evaporated and the crude product is purified by CC on silica gel eluting with heptane: EA 7:3 to give 3-ethyl-5-methyl-4-oxiranylmethoxy-benzonitrile (5.85 g) as a yellow oil; LC-MS: $t_R$=0.96 min; [M+42]$^+$=259.08.

b) The above epoxide is dissolved in 7 N NH$_3$ in methanol (250 mL) and the solution is stirred at 65° C. for 18 h. The solvent is evaporated to give crude (S)-4-(3-amino-2-hydroxypropoxy)-3-ethyl-5-methylbenzonitrile (6.23 g) as a yellow oil; LC-MS: $t_R$=0.66 min; [M+1]$^+$=235.11.

N—((S)-3-[2-Ethyl-4-(N-hydroxycarbamimidoyl)-6-methyl-phenoxy]-2-hydroxy-propyl)-2-hydroxy-acetamide a) To a solution of (S)-4-(3-amino-2-hydroxypropoxy)-3-ethyl-5-methylbenzonitrile (6.23 g, 26.59 mmol) in THF (150 mL), glycolic acid (2.43 g, 31.9 mmol), HOBt (4.31 g, 31.9 mmol), and EDC hydrochloride (6.12 g, 31.9 mmol) are added. The mixture is stirred at rt for 18 h before it is diluted with sat. aq. NaHCO$_3$ and extracted twice with EA. The combined org. extracts are dried over MgSO$_4$, filtered and concentrated. The crude product is purified by CC with DCM containing 8% of methanol to give (S)—N-[3-(4-cyano-2-ethyl-6-methyl-phenoxy)-2-hydroxy-propyl]-2-hydroxy-acetamide (7.03 g) as a yellow oil; LC-MS: $t_R$=0.74 min, [M+1]$^+$=293.10; $^1$H NMR (CDCl$_3$): δ 1.25 (t, J=7.5 Hz, 3H), 2.32 (s, 3H), 2.69 (q, J=7.5 Hz, 2H), 3.48-3.56 (m, 3H), 3.70-3.90 (m, 3H), 4.19 (s, br, 3H), 7.06 (m, 1H), 7.36 (s, 1H), 7.38 (s, 1H).

b) The above nitrile is converted to the N-hydroxy-benzamidine according to literature procedures (e.g. E. Meyer, A. C. Joussef, H. Gallardo, *Synthesis* 2003, 899-905); LC-MS: $t_R$=0.51 min, [M+1]$^+$=326.13; $^1$H NMR (D$_6$-DMSO): δ 1.17 (t, J=7.4 Hz, 3H), 2.24 (s, 3H), 2.62 (q, J=7.4 Hz, 2H), 3.23 (m, 1H), 3.43 (m, 1H), 3.67 (m, 2H), 3.83 (s, 2H), 3.93 (m, 1H), 5.27 (s br, 1H), 5.58 (s br, 1H), 5.70 (s, 2H), 7.34 (s, 1H), 7.36 (s, 1H), 7.67 (m, 1H), 9.46 (s br, 1H).

(S)—N-(3-[2-Chloro-4-(N-hydroxycarbamimidoyl)-6-methyl-phenoxy]-2-hydroxy-propyl)-2-hydroxy-acetamide The title compound is obtained as a beige wax (1.1 g) in analogy to N—((S)-3-[2-ethyl-4-(N-hydroxycarbamimidoyl)-6-methyl-phenoxy]-2-hydroxy-propyl)-2-hydroxy-acetamide starting from 3-chloro-4-hydroxy-5-methyl-benzonitrile; LC-MS: $t_R$=0.48 min, [M+H]$^+$=331.94.

3-Chloro-N-hydroxy-4-methanesulfonylamino-5-methyl-benzamidine a) A mixture of 4-amino-3-chloro-5-methylbenzonitrile (155 mg, 930 μmol) and methanesulfonylchloride (2.13 g, 18.6 mmol, 1.44 mL) is heated under microwave conditions to 150° C. for 7 h. The mixture is cooled to rt, diluted with water and extracted with EA. The org. extract is dried over MgSO$_4$, filtered and concentrated. The crude product is purified on prep. TLC using heptane:EA 1:1 to give N-(2-chloro-4-cyano-6-methyl-phenyl)-methanesulfonamide (105 mg) as an orange solid; LC-MS**: $t_R$=0.48 min; $^1$H NMR (CDCl$_3$): δ2.59 (s, 3H), 3.18 (s, 3H), 6.27 (s, 1H), 7.55 (d, J=1.3 Hz, 1H), 7.65 (d, J=1.5 Hz, 1H).

b) Hydroxylamine hydrochloride (60 mg, 858 μmol) and NaHCO$_3$ (72 mg, 858 μmol) is added to a solution of N-(2-chloro-4-cyano-6-methyl-phenyl)-methanesulfonamide (105 mg, 429 μmol) in methanol (10 mL). The mixture is stirred at 65° C. for 18 h. The solvent is removed in vacuo and the residue is dissolved in a small volume of water (2 mL) and extracted three times with EA (15 mL). The combined org. extracts are dried over MgSO$_4$, filtered, concentrated and dried to give the title compound (118 mg) as a white solid; LC-MS**: $t_R$=0.19 min, [M+1]$^+$=277.94; $^1$H NMR (CDCl$_3$): δ2.57 (s, 3H), 3.13 (s, 3H), 6.21 (s, 1H), 7.49 (d, J=1.5 Hz, 1H), 7.63 (d, J=1.5 Hz).

3-Ethyl-N-hydroxy-4-methanesulfonylamino-5-methyl-benzamidine a) In a 2.5 L three-necked round-bottom flask 2-ethyl-6-methyl aniline (250 g, 1.85 mol) is dissolved in DCM (900 mL) and cooled to 5-10° C. Bromine (310.3 g, 1.94 mol) is added over a period of 105 min such as to keep the temperature at 5-15° C. An aq. 32% NaOH solution (275 mL) is added over a period of 10 min to the greenish-grey suspension while keeping the temperature of the reaction mixture below 25° C. DCM (70 mL) and water (100 mL) are added and the phases are separated. The aq. phase is extracted with DCM (250 mL). The combined org. phases are washed with water (300 mL) and concentrated at 50° C. to afford the 4-bromo-2-ethyl-6-methyl-aniline (389 g) as a brown oil; $^1$H NMR (CDCl$_3$): δ 1.27 (t, J=7.3 Hz, 3H), 2.18 (s, 3H), 2.51 (q, J=7.3 Hz, 2H), 3.61 (s br, 1H), 7.09 (s, 2H).

b) A double-jacketed 4 L-flask is charged with 4-bromo-2-ethyl-6-methyl-aniline (324 g, 1.51 mol), sodium cyanide (100.3 g, 1.97 mol), potassium iodide (50.2 g, 0.302 mol) and copper(I)iodide (28.7 g, 0.151 mol). The flask is evacuated three times and refilled with nitrogen. A solution of N,N'-dimethylethylenediamine (191.5 mL, 1.51 mol) in toluene (750 mL) is added. The mixture is heated to 118° C. and stirred at this temperature for 21 h. The mixture is cooled to 93° C. and water (1250 mL) is added to obtain a solution. Ethyl acetate (1250 mL) is added at 22-45° C. and the layers are separated. The org. phase is washed with 10% aq. citric acid (2×500 mL) and water (500 mL). The separated org. phase is evaporated to dryness to afford 4-amino-3-ethyl-5-methyl-benzonitrile (240 g) as a metallic black solid; $^1$H NMR (CDCl$_3$): δ1.29 (t, J=7.5 Hz, 3H), 2.19 (s, 3H), 2.52 (q, J=7.3 Hz, 2H), 4.10 (s br, 1H), 7.25 (s, 2H).

c) The title compound is then prepared from the above 4-amino-3-ethyl-5-methyl-benzonitrile in analogy to 3-chloro-N-hydroxy-4-methanesulfonylamino-5-methyl-benzamidine; LC-MS**: $t_R$=0.26 min, [M+1]$^+$=272.32.

3-Chloro-4-ethanesulfonylamino N-hydroxy-5-methyl-benzamidine

The title compound is prepared in analogy to 3-chloro-N-hydroxy-4-methanesulfonylamino-5-methyl-benzamidine using ethanesulfonylchloride; LC-MS**: $t_R$=0.27 min, [M+1]$^+$=292.13; $^1$H NMR (D$_6$-DMSO): δ 1.36 (t, J=7.5 Hz, 3H), 2.40 (s, 3H), 3.22 (q, J=7.5 Hz), 5.88 (s, 2H), 7.57 (d, J=1.5 Hz, 1H), 7.63 (d, J=1.5 Hz, 1H), 9.18 (s, 1H), 9.78 (s, 1H).

4-Benzyloxy-3-ethyl-5-methyl-benzoic acid a) To a solution of 3-ethyl-4-hydroxy-5-methyl-benzaldehyde (34.9 g, 0.213 mol, prepared from 2-ethyl-6-methylphenol according to the literature cited for 3-ethyl-4,N-dihydroxy-5-methyl-benzamidine) in MeCN (350 mL), $K_2CO_3$ (58.7 g, 0.425 mol) and benzylbromide (36.4 g, 0.213 mol) are added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde (45 g) as an orange oil. $^1$H NMR (CDCl$_3$): δ1.29 (t, J=7.5 Hz, 3H), 2.40 (s, 3H), 2.77 (q, J=7.8 Hz, 2H), 4.90 (s, 2H), 7.31-7.52 (m, 5H), 7.62 (d, J=1.5 Hz, 1H), 7.66 (d, J=1.8 Hz, 1H), 9.94 (s, 1H).

b) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of $NaH_2PO_4$ dihydrate (249 g, 2.08 mol) in water (1500 mL) is added. To this mixture, $NaClO_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted three times with 0.5 N aq. NaOH (1000 mL), the aq. phase is acidified with 25% aq. HCl (500 mL) and extracted twice with TBME (1000 mL). These org. extracts are combined and evaporated to dryness to give the title compound; $^1$H NMR (D$_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

Example 1

(S)-3-(2-Ethyl-4-{5-[2-(1-ethyl-propyl)-6-methoxy-pyridin-4-yl]-[1,2,4]oxadiazol-3-yl}-6-methyl-phenoxy)-propane-1,2-diol a) To a solution of 2-(1-ethyl-propyl)-6-methoxy-isonicotinic acid (190 mg, 732 μmol) in THF (10 mL) and DMF (2 mL), DIPEA (190 mg, 1.46 mmol) followed by TBTU (235 mg, 732 μmol) is added. The mixture is stirred at rt for 10 min before (R)-4-(2,2-dimethyl-[1,3]dioxolan-4-ylmethoxy)-3-ethyl-N-hydroxy-5-methyl-benzamidine 226 mg, 732 μmol) is added. The mixture is stirred at rt for 1 h before it is diluted with EA and washed with water. The org. phase is separated and concentrated. The remaining residue is dissolved in dioxane (10 mL) and heated to 105° C. for 18 h. The mixture is cooled to rt, concentrated and the crude product is purified on prep. TLC plates using DCM containing 10% of methanol to give 4-{3-[4-((R)-2,2-dimethyl-[1,3]dioxolan-4-ylmethoxy)-3-ethyl-5-methyl-phenyl]-[1,2,4]oxadiazol-5-yl}-2-(1-ethyl-propyl)-6-methoxy-pyridine (256 mg) as a yellow oil; LC-MS: $t_R$=1.28 min, [M+H]$^+$=496.23.

b) A solution of 4-{3-[4-((R)-2,2-dimethyl-[1,3]dioxolan-4-ylmethoxy)-3-ethyl-5-methyl-phenyl]-[1,2,4]oxadiazol-5-yl}-2-(1-ethyl-propyl)-6-methoxy-pyridine (250 mg, 504 μmol) in 4 M HCl in dioxane (10 mL) is stirred at rt for 90 min before it is concentrated. The crude product is purified on prep. TLC plates using DCM containing 10% of methanol to give the title compound (76 mg) as a pale brownish solid; LC-MS: $t_R$=1.12 min, [M+H]$^+$=456.12; $^1$H NMR (CDCl$_3$): δ0.85 (t, J=7.0 Hz, 6H), 1.33 (t, J=7.0 Hz, 3H), 1.70-1.89 (m, 4H), 2.42 (s, 3H), 2.61-2.71 (m, 1H), 2.78 (q, J=7.3 Hz, 2H), 3.82-4.00 (m, 4H), 4.04 (s, 3H), 4.14-4.21 (m, 1H), 7.34 (s, 1H), 7.46 (s, 1H), 7.86-7.91 (m, 2H).

Example 2

(S)-3-{4-[5-(2-Cyclopentyl-6-methoxy-pyridin-4-yl)-[1,2,4]oxadiazol-3-yl]-2-ethyl-6-methyl-phenoxy}-propane-1,2-diol The title compound is prepared in analogy to Example 1 starting from 2-cyclopentyl-6-methoxy-isonicotinic acid; LC-MS: $t_R$=1.14 min, [M+H]$^+$=454.16; $^1$H NMR (CDCl$_3$): δ1.33 (t, J=7.5 Hz, 3H), 1.72-1.78 (m, 2H), 1.85-1.94 (m, 4H), 2.03-2.15 (m, 2H), 2.41 (s, 3H), 2.72 (d, J=5.3 Hz, 1H), 2.77 (q, J=7.5 Hz, 2H), 3.19-3.28 (m, 1H), 3.81-3.94 (m, 2H), 3.95-3.98 (m, 2H), 4.02 (s, 3H), 4.14-4.21 (m, 1H), 7.31 (d, J=1.3 Hz, 1H), 7.51 (d, J=1.0 Hz, 1H), 7.88 (d, J=1.8 Hz), 7.89 (d, J=2.0 Hz, 1H).

Example 3

(R)-3-{4-[5-(2-Cyclopentyl-6-methoxy-pyridin-4-yl)-[1,2,4]oxadiazol-3-yl]-2-ethyl-6-methyl-phenoxy}-propane-1,2-diol a) A solution of 2-cyclopentyl-6-methoxy-isonicotinic acid (21.0 g, 102 mmol), 3-ethyl-4,N-dihydroxy-5-methyl-benzamidine (20.0 g, 103 mmol) and HOBt (1.24 g, 9 mmol) in THF (200 mL) is cooled to 5° C. before a solution of DCC (20.0 g, 97 mmol) in THF (100 mL) is added dropwise. Upon complete addition, the mixture is stirred at rt for 18 h then at 75° C. for 48 h. The solvent is evaporated and the remaining residue is dissolved in TBME (200 mL). The precipitate that forms is removed, filtered off and washed with additional TBME (200 mL). The filtrate is washed with approximately 4% aq. NaHCO$_3$ solution (100 mL) and water (100 mL) and concentrated. The crude product is recrystallised from hot acetonitrile (200 mL) to give 4-[5-(2-cyclopentyl-6-methoxy-pyridin-4-yl)-[1,2,4]oxadiazol-3-yl]-2-ethyl-6-methyl-phenol (28.6 g) as a white solid; $^1$H NMR (CDCl$_3$): δ1.33 (t, J=7.5 Hz, 3H), 1.70-1.80 (m, 2H), 1.84-1.96 (m, 4H), 2.05-2.16 (m, 2H), 2.36 (s, 3H), 2.74 (q, J=7.3 Hz, 2H), 3.25 (quint, J=7.5 Hz, 1H), 4.02 (s, 3H), 5.01 (s), 7.31 (s, 1H), 7.51 (s, 1H), 7.85 (s, 2H).

b) A mixture of 4-[5-(2-cyclopentyl-6-methoxy-pyridin-4-yl)-[1,2,4]oxadiazol-3-yl]-2-ethyl-6-methyl-phenol (250 mg, 659 μmol), (R)-3-chloro-1,2-propanediol (609 mg, 6.59 mmol) in isopropanol (8 mL) and 3 M aq. NaOH (2 mL) is stirred at 60° C. for 15 h. The mixture is diluted with EA and washed with brine, 1 M aq. NaOH and again with brine. The org. extract is dried over Na$_2$SO$_4$, filtered and concentrated. The crude product is purified on prep. TLC plates using DCM containing 10% of methanol to give the title compound (297 mg) as a pale yellow oil; LC-MS**: $t_R$=0.87 min, [M+H]$^+$=454.26.

Example 4

(S)-3-{4-[5-(2-Cyclohexyl-6-methoxy-pyridin-4-yl)-[1,2,4]oxadiazol-3-yl]-2-ethyl-6-methyl-phenoxy}-propane-1,2-diol The title compound is prepared in analogy to Example 3 starting from 2-cyclohexyl-6-methoxy-isonicotinic acid, 3-ethyl-4,N-dihydroxy-5-methyl-benzamidine and (S)-3- chloro-1,2-propanediol; LC-MS: $t_R$=1.16 min, [M+H]$^+$=468.08; $^1$H NMR (CDCl$_3$): δ1.33 (t, J=7.5 Hz, 3H), 1.34-1.40 (m, 1H), 1.40-1.52 (m, 2H), 1.57-1.69 (m, 2H), 1.77-1.84 (m, 1H), 1.87-1.95 (m, 2H), 1.99-2.08 (m, 2H), 2.41 (s, 3H), 2.70-2.81 (m, 3H), 3.83-4.00 (m, 4H), 4.03 (s, 3H), 4.15-4.21 (m, 1H), 7.32 (s, 1H), 7.49 (s, 1H), 7.88 (s, 1H), 7.90 (s, 1H).

Example 5

Ethanesulfonic acid {2-chloro-4-[5-(2-cyclopentyl-6-methoxy-pyridin-4-yl)-[1,2,4]oxadiazol-3-yl]-6-methyl-phenyl}-amide The title compound (65 mg) is obtained as an off-white solid in analogy to Example 11 starting from 2-cyclopentyl-6-methoxy-isonicotinic acid (55 mg, 249 µmol) and 3-chloro-4-ethanesulfonylamino N-hydroxy-5-methyl-benzamidine (73 mg, 249 µmol); LC-MS**: $t_R$=0.93 min, [M+H]$^+$=477.13; $^1$H NMR (CDCl$_3$): δ1.52 (t, J=7.3 Hz, 3H), 1.70-1.80 (m, 2H), 1.84-1.95 (m, 4H), 2.06-2.17 (m, 2H), 2.65 (s, 3H), 3.20-3.28 (m, 1H), 3.32 (q, J=7.3 Hz, 2H), 4.02 (s, 3H), 6.14 (s, 1H), 7.30 (s, 1H), 7.49 (s, 1H), 8.05 (s, 1H), 8.14 (s, 1H).

Example 6

N-[(2S)-3-(2-Ethyl-4-{5-[2-(1-ethyl-propyl)-6-methoxy-pyridin-4-yl]-[1,2,4]oxadiazol-3-yl}-6-methyl-phenoxy)-2-hydroxy-propyl]-2-hydroxy-acetamide To a solution of 2-(1-ethyl-propyl)-6-methoxy-isonicotinic acid (200 mg, 770 µmol) in DMF (3 mL) and THF (10 mL), DIPEA (200 mg, 1.54 mmol) and TBTU (272 mg, 847 µmol) are added. The mixture is stirred at rt for 10 min before N—((S)-3-[2-ethyl-4-(N-hydroxycarbamimidoyl)-6-methyl-phenoxy]-2-hydroxy-propyl)-2-hydroxy-acetamide (251 mg, 770 µmol) is added. The mixture is stirred at rt for 30 min, diluted with EA (100 mL) and washed with brine. The org. extract is concentrated and the residue is dissolved in dioxane (50 mL). The mixture is stirred at 100° C. for 2 h before it is concentrated. The crude product is purified on prep. TLC plates using DCM containing 10% of methanol to give the title compound (180 mg) as a resin; LC-MS: $t_R$=1.08 min, [M+H]$^+$=513.13; $^1$H NMR (CDCl$_3$): δ0.84 (t, J=7.3 Hz, 6H), 1.31 (t, J=7.5 Hz, 3H), 1.68-1.88 (m, 4H), 2.38 (s, 3H), 2.55-2.64 (m, 1H), 2.74 (q, J=7.5 Hz, 2H), 3.50-3.58 (m, 1H), 3.74-3.94 (m, 4H), 4.01 (s, 3H), 4.17-4.25 (m, 3H), 7.09 (t br, J=5.5 Hz, 1H), 7.31 (d, J=1.3 Hz, 1H), 7.43 (d, J=1.3 Hz, 1H), 7.86 (d, J=1.8 Hz, 1H), 7.88 (d, J=2.0 Hz).

Example 7

N-((2S)-3-{4-[5-(2-Cyclopentyl-6-methoxy-pyridin-4-yl)-[1,2,4]oxadiazol-3-yl]-2-ethyl-6-methyl-phenoxy}-2-hydroxy-propyl)-2-hydroxy-acetamide The title compound is prepared in analogy to Example 6 starting from 2-cyclopentyl-6-methoxy-isonicotinic acid; LC-MS: $t_R$=1.09 min, [M+H]$^+$=511.17; $^1$H NMR (CDCl$_3$): δ1.32 (t, J=7.8 Hz, 3H), 1.68-1.79 (m, 2H), 1.83-1.94 (m, 4H), 2.06-2.14 (m, 2H), 2.39 (s, 3H), 2.75 (q, J=7.8 Hz, 2H), 3.20-3.29 (m, 1H), 3.49-3.57 (m, 1H), 3.75-3.92 (m, 3H), 4.01 (s, 3H), 4.18-4.23 (m, 3H), 7.14 (s br, 1H), 7.30 (s, 1H), 7.50 (s, 1H), 7.86 (s, 1H), 7.87 (s, 1H).

Example 8

N-((2S)-3-{4-[5-(2-Cyclohexyl-6-methoxy-pyridin-4-yl)-[1,2,4]oxadiazol-3-yl]-2-ethyl-6-methyl-phenoxy}-2-hydroxy-propyl)-2-hydroxy-acetamide The title compound is prepared in analogy to Example 6 starting from 2-cyclohexyl-6-methoxy-isonicotinic acid; LC-MS: $t_R$=1.21 min, [M+H]$^+$=525.15; $^1$H NMR (CDCl$_3$): δ1.26-1.39 (m, 4H), 1.39-1.52 (m, 2H), 1.56-1.69 (m, 2H), 1.76-1.83 (m, 1H), 1.86-1.95 (m, 2H), 1.99-2.06 (m, 2H), 2.38 (s, 3H), 2.69-2.79 (m, 3H), 3.51-3.58 (m, 1H), 3.75-3.93 (m, 3H), 4.02 (s, 3H), 4.17-4.24 (m, 3H), 7.16 (s br, 1H), 7.30 (s, 1H), 7.48 (s, 1H), 7.85 (s, 1H), 7.87 (s, 1H).

Example 9

N-[(2S)-3-(2-Ethyl-4-{5-[2-(1-ethyl-propyl)-6-methoxy-pyridin-4-yl]-[1,2,4]oxadiazol-3-yl}-6-methyl-phenoxy)-2-hydroxy-propyl]-2-hydroxy-N-methyl-acetamide a) To a solution of 2-(1-ethyl-propyl)-6-methoxy-isonicotinic acid (436 mg, 1.95 mmol) and DIPEA (759 mg, 5.86 mmol) in DMF (30 mL), TBTU (627 mg, 1.95 mmol) is added. The mixture is stirred at rt for 15 min before 3-ethyl-4,N-dihydroxy-5-methyl-benzamidine (379 mg, 1.95 mmol) is added. Stirring is continued at rt for 2 h. The mixture is diluted with DCM (100 mL) and washed three times with sat. aq. NaHCO$_3$ solution. The org. extract is dried over MgSO$_4$, filtered and concentrated. The residue is dissolved in dioxane (20 mL) and the mixture is stirred at 100° C. for 18 h. The mixture is concentrated and the crude product is purified by prep. HPLC to give 2-ethyl-4-{5-[2-(1-ethyl-propyl)-6-methoxy-pyridin-4-yl]-[1,2,4]oxadiazol-3-yl}-6-methyl-phenol (355 mg) as a beige solid; LC-MS: $t_R$=1.20 min, [M+H]$^+$=382.04; $^1$H NMR (CDCl$_3$): δ0.84 (t, J=7.3 Hz, 6H), 1.34 (t, J=7.5 Hz, 3H), 1.68-1.89 (m, 4H), 2.36 (s, 3H), 2.57-2.65 (m, 1H), 2.74 (q, J=7.8 Hz, 2H), 4.02 (s, 3H), 5.00 (s br, 1H), 7.33 (s, 1H), 7.45 (s, 1H), 7.85 (s, 2H).

b) A mixture of 2-ethyl-4-{5-[2-(1-ethyl-propyl)-6-methoxy-pyridin-4-yl]-[1,2,4]oxadiazol-3-yl}-6-methyl-phenol (355 mg, 931 µmol) and (R)-epichlorohydrine (861 mg, 9.31 mmol) in 3 M aq. NaOH (4 mL) and isopropanol (15 mL) is stirred at rt for 18 h before a second portion of (R)-epichlorohydrine (430 mg, 4.65 mmol) is added. Stirring is continued at rt for 8 h. The mixture is diluted with EA (100 mL) and washed twice with 1 N aq. NaOH solution (2×15 mL) followed by brine (25 mL). The org. extract is dried over MgSO$_4$, filtered and concentrated. The crude product is purified by prep. HPLC to give 4-[(2S)-3-(3-ethyl-5-methyl-4-oxiranylmethoxy-phenyl)-[1,2,4]oxadiazol-5-yl]-2-(1-ethyl-propyl)-6-methoxy-pyridine (272 mg) as a white powder; LC-MS: $t_R$=1.25 min, [M+H]$^+$=438.09.

c) A solution of the above epoxide (267 mg, 610 µmol) in 2 M methylamine in methanol (15 mL) is stirred in a sealed vial at 60° C. for 3 h. The mixture is concentrated and the crude product is purified on prep. TLC plates using DCM containing 10% of methanol to give (2S)-1-(2-ethyl-4-{5-[2-(1-ethyl-propyl)-6-methoxy-pyridin-4-yl]-[1,2,4]oxadiazol-3-yl}-6-methyl-phenoxy)-3-methylamino-propan-2-ol (299 mg) as a beige solid; LC-MS: $t_R$=0.96 min, [M+H]$^+$=469.12; $^1$H NMR (CDCl$_3$): δ0.84 (t, J=7.3 Hz, 6H), 1.33 (t, J=7.5 Hz, 3H), 1.69-1.88 (m, 4H), 2.41 (s, 3H), 2.55 (s, 3H), 2.57-2.64 (m, 1H), 2.78 (q, J=7.5 Hz, 2H), 2.85-2.94 (m, 2H), 3.89 (d, J=5.0 Hz, 2H), 4.02 (s, 3H), 4.14-4.20 (m, 1H), 7.32 (d, J=1.3 Hz, 1H), 7.44 (d, J=1.3 Hz, 1H), 7.87 (d, J=2.0 Hz), 7.89 (d, J=1.8 Hz, 1H).

d) EDC hydrochloride (144 mg, 753 μmol) is added to a stirred solution of (2S)-1-(2-ethyl-4-{5-[2-(1-ethyl-propyl)-6-methoxy-pyridin-4-yl]-[1,2,4]oxadiazol-3-yl}-6-methyl-phenoxy)-3-methylamino-propan-2-ol (294 mg, 627 μmol), glycolic acid (57 mg, 753 μmol) and HOBt (101 mg, 753 μmol) in THF (10 mL). The mixture is stirred at rt for 2 h before it is concentrated. The crude product is purified by prep. HPLC, then on prep. TLC plates using DCM containing 10% of 7 N NH$_3$ in methanol to give the title compound (149 mg) as a white solid; LC-MS: $t_R$=1.14 min, [M+H]$^+$=527.17; $^1$H NMR (CDCl$_3$): δ0.84 (t, J=7.5 Hz, 6H), 1.33 (t, J=7.5 Hz, 3H), 1.69-1.88 (m, 4H), 2.40 (s, 3H), 2.57-2.66 (m, 1H), 2.76 (q, J=7.5 Hz, 2H), 3.10 (s, 3H), 3.76 (d, J=5.3 Hz, 2H), 3.80-3.88 (m, 1H), 3.89-3.94 (m, 1H), 4.02 (s, 3H), 4.25 (s, 2H), 4.28-4.36 (m, 1H), 7.33 (s, 1H), 7.45 (s, 1H), 7.88 (s, 1H), 7.89 (s, 1H).

Example 10

N-((2S)-3-{4-[5-(2-Cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide The title compound is prepared in analogy to Example 9 starting from 2-cyclopentyl-6-methoxy-isonicotinic acid; LC-MS: $t_R$=1.15 min, [M+H]$^+$=525.14; $^1$H NMR (CDCl$_3$): δ1.30 (t, J=7.5 Hz, 3H), 1.67-1.77 (m, 2H), 1.82-1.94 (m, 4H), 2.05-2.14 (m, 2H), 2.37 (s, 3H), 2.74 (q, J=7.5 Hz), 3.07 (s, 3H), 3.18-3.27 (m, 1H), 3.71-3.76 (m, 2H), 3.79-3.85 (m, 1H), 3.85-3.91 (m, 1H), 3.99 (s, 3H), 4.23 (s, 2H), 4.26-4.34 (m, 1H), 7.27 (s), 7.48 (s, 1H), 7.84 (s, 1H), 7.86 (s, 1H).

Example 11

N-(2-Chloro-4-{5-[2-(1-ethyl-propyl)-6-methoxy-pyridin-4-yl]-[1,2,4]oxadiazol-3-yl}-6-methyl-phenyl)-methanesulfonamide HOBt (20 mg, 148 μmol) and EDC HCl (28 mg, 148 μmol) are added to a solution of 2-(1-ethyl-propyl)-6-methoxy-isonicotinic acid (30 mg, 134 μmol) in DMF (5 mL). The mixture is stirred at rt for 5 min before 3-chloro-N-hydroxy-4-methanesulfonylamino-5-methyl-benzamidine (38 mg, 136 μmol) is added. The mixture is stirred at rt for 18 h before it is diluted with sat. aq. NaHCO$_3$ solution and extracted twice with EA. The combined org. extracts are dried over MgSO$_4$, filtered and concentrated. The resulting orange oil (65 mg) is dissolved in dioxane (5 mL) and heated to 80° C. for 3 h. The solvent is removed in vacuo and the crude product is purified on prep. TLC plates using heptane:EA 3:2 to give the title compound (36 mg) as a white solid; LC-MS**: $t_R$=0.88 min, [M+H]$^+$=465.06; $^1$H NMR (CDCl$_3$): δ0.84 (t, J=7.5 Hz, 6H), 1.69-1.88 (m, 4H), 2.56-2.63 (m, 1H), 2.65 (s, 3H), 3.17 (s, 3H), 4.02 (s, 3H), 6.26 (s, 1H), 7.32 (d, J=1.0 Hz, 1H), 7.43 (d, J=0.8 Hz, 1H), 8.07 (d, J=1.0 Hz, 1H), 8.17 (d, J=1.5 Hz, 1H).

Example 12

N-{2-Chloro-4-[5-(2-cyclopentyl-6-methoxy-pyridin-4-yl)-[1,2,4]oxadiazol-3-yl]-6-methyl-phenyl}-methanesulfonamide The title compound is prepared in analogy to Example 11 starting from 2-cyclopentyl-6-methoxy-isonicotinic acid; LC-MS**: $t_R$=0.92 min, [M+H]$^+$=463.01; $^1$H NMR (CDCl$_3$): δ 1.70-1.80 (m, 2H), 1.84-1.95 (m, 4H), 2.06-2.16 (m, 2H), 2.65 (s, 3H), 3.17 (s, 3H), 3.20-3.29 (m, 1H), 4.03 (s, 3H), 6.24 (s, 1H), 7.30 (d, J=1.0 Hz, 1H), 7.50 (d, J=1.0 Hz, 1H), 8.07 (d, J=1.3 Hz, 1H), 8.16 (d, J=1.5 Hz, 1H).

Example 13

(S)-3-{2-Chloro-4-[5-(2-cyclopentyl-6-methoxy-pyridin-4-yl)-[1,2,4]oxadiazol-3-yl]-6-methyl-phenoxy}-propane-1,2-diol The title compound is prepared in analogy to Example 1 starting from 2-cyclopentyl-6-methoxy-isonicotinic acid and (R)-3-chloro-4-(2,2-dimethyl-[1,3]dioxolan-4-ylmethoxy)-N-hydroxy-5-methyl-benzamidine; LC-MS**: $t_R$=0.89 min, [M+H]$^+$=460.18; $^1$H NMR (CDCl$_3$): δ 1.72-1.80 (m, 2H), 1.84-1.95 (m, 4H), 2.03 (t br, J=5.8 Hz, 1H), 2.07-2.16 (m, 2H), 2.45 (s, 3H), 2.80 (d br, J=5.0 Hz, 1H), 3.20-3.29 (m, 1H), 3.83-3.93 (m, 2H), 4.02 (s, 3H), 4.11-4.14 (m, 2H), 4.15-4.21 (m, 1H), 7.30 (d, J=1.0 Hz, 1H), 7.50 (d, J=0.8 Hz, 1H), 7.95 (d, J=1.8 Hz, 1H), 8.09 (d, J=1.8 Hz, 1H).

Example 14

N-((2S)-3-{2-Chloro-4-[5-(2-cyclopentyl-6-methoxy-pyridin-4-yl)-[1,2,4]oxadiazol-3-yl]-6-methyl-phenoxy}-2-hydroxy-propyl)-2-hydroxy-acetamide The title compound (135 mg) is prepared in analogy to Example 6 starting from 2-cyclopentyl-6-methoxy-isonicotinic acid (100 mg, 452 μmol) and (S)—N-(3-[2-chloro-4-(N-hydroxycarbamimidoyl)-6-methyl-phenoxy]-2-hydroxy-propyl)-2-hydroxy-acetamide (150 mg, 452 μmol): LC-MS**: $t_R$=0.85 min, [M+H]$^+$=517.21; $^1$H NMR (CDCl$_3$): δ1.69-1.80 (m, 2H), 1.83-1.95 (m, 4H), 2.06-2.15 (m, 2H), 2.42 (s, 3H), 3.19-3.29 (m, 1H), 3.53-3.61 (m, 1H), 3.81 (ddd, J=14.1, 6.5, 3.5 Hz, 1H), 3.97-4.01 (m, 1H), 4.01 (s, 3H), 4.06 (dd, J=9.5, 4.8 Hz, 1H), 4.21 (s, 2H), 4.21-4.26 (m, 1H), 7.12 (t br, J=6.0 Hz, 1H), 7.27 (d, J=1.3 Hz, 1H), 7.48 (d, J=1.0 Hz, 1H), 7.92 (d, J=1.5 Hz, 1H), 8.05 (d, J=1.8 Hz, 1H).

Example 15

(S)-3-(2-Ethyl-4-{5-[2-methoxy-6-(3-methyl-butyl)-pyridin-4-yl]-[1,2,4]oxadiazol-3-yl}-6-methyl-phenoxy)-propane-1,2-diol The title compound is prepared in analogy to Example 1 starting from 2-methoxy-6-(3-methyl-butyl)-isonicotinic acid and (R)-4-(2,2-dimethyl-[1,3]dioxolan-4-ylmethoxy)-3-ethyl-N-hydroxy-5-methyl-benzamidine; LC-MS: $t_R$=1.14 min, [M+H]$^+$=456.16; $^1$H NMR (CDCl$_3$): δ 1.00 (d, J=6.3 Hz, 6H), 1.33 (t, J=7.5 Hz, 3H), 1.64-1.74 (m, 3H), 2.41 (s, 3H), 2.77 (q, J=7.5 Hz, 2H), 2.81-2.86 (m, 2H), 3.82-3.94 (m, 2H), 3.94-3.98 (m, 2H), 4.03 (s, 3H), 4.14-4.21 (m, 1H), 7.32 (d, J=0.8 Hz, 1H), 7.49 (d, J=0.8 Hz, 1H), 7.88 (s, 1H), 7.89 (s, 1H).

Example 16

N-[(2S)-3-(2-Ethyl-4-{5-[2-methoxy-6-(3-methyl-butyl)-pyridin-4-yl]-[1,2,4]oxadiazol-3-yl}-6-methyl-phenoxy)-2-hydroxy-propyl]-2-hydroxy-acetamide The title compound (12 mg) is prepared in analogy to Example 6 starting from 2-methoxy-6-(3-methyl-butyl)- isonicotinic acid (60 mg, 269 μmol) and (S)—N-(3-[2-chloro-4-(N-hydroxycarbamimidoyl)-6-methyl-phenoxy]-2-hydroxy-propyl)-2-hydroxy-acetamide (87 mg, 269 μmol): LC-MS: $t_R$=1.10 min, [M+H]$^+$=513.23; $^1$H NMR (CDCl$_3$): δ1.00 (d, J=6.3 Hz, 6H), 1.32 (t, J=7.8 Hz, 3H), 1.64-1.73 (m, 3H), 2.40 (s, 3H), 2.76 (q, J=7.5 Hz, 2H), 2.81-2.87 (m, 2H), 3.49-3.58 (m, 1H), 3.77-3.94 (m, 3H), 4.03 (s, 3H), 4.19-4.25 (m, 3H), 7.00 (t br, J=6.0 Hz, 1H), 7.32 (d, J=0.5 Hz, 1H), 7.49 (d, J=0.8 Hz, 1H), 7.87 (s, 1H), 7.88 (s, 1H).

Example 17

N-{2-Chloro-4-[5-(2-cyclohexyl-6-methoxy-pyridin-4-yl)-[1,2,4]oxadiazol-3-yl]-6-methyl-phenyl}-methanesulfonamide The title compound is prepared in analogy to Example 11 starting from 2-cyclohexyl-6-methoxy-isonicotinic acid; LC-MS**: $t_R$=0.94 min, [M+H]$^+$=477.12; $^1$H NMR (CDCl$_3$): δ 1.27-1.68 (m, 5H), 1.77-1.84 (m, 1H), 1.88-1.95 (m, 2H), 2.00-2.07 (m, 2H), 2.65 (s, 3H), 2.75 (tt, J=11.5, 3.3 Hz, 1H), 3.17 (s, 3H), 4.03 (s, 3H), 6.23 (s, 1H), 7.31 (d, J=1.0 Hz, 1H), 7.48 (d, J=0.8 Hz, 1H), 8.07 (d, J=1.3 Hz, 1H), 8.17 (d, J=1.8 Hz, 1H).

Example 18

N-(2-Ethyl-4-{5-[2-(1-ethyl-propyl)-6-methoxy-pyridin-4-yl]-[1,2,4]oxadiazol-3-yl}-6-methyl-phenyl)-methanesulfonamide The title compound (24 mg) is prepared in analogy to Example 11 starting from 2-(1-ethyl-propyl)-6-methoxy-isonicotinic acid (32 mg, 143 μmol) and 3-ethyl-N-hydroxy-4-methanesulfonylamino-5-methyl-benzamidine (40 mg, 150 mmol); LC-MS**: $t_R$=0.91 min, [M+H]$^+$=459.09; $^1$H NMR (CDCl$_3$): δ0.85 (t, J=7.3 Hz, 6H), 1.36 (t, J=7.3 Hz, 3H), 1.69-1.89 (m, 4H), 2.56 (s, 3H), 2.57-2.65 (m, 1H), 2.93 (q, J=7.5 Hz, 2H), 3.18 (s, 3H), 4.02 (s, 3H), 5.92 (s, 1H), 7.33 (s, 1H), 7.44 (s, 1H), 7.97 (s, 1H), 7.99 (s, 1H).

Example 19

N-{4-[5-(2-Cyclopentyl-6-methoxy-pyridin-4-yl)-[1,2,4]oxadiazol-3-yl]-2-ethyl-6-methyl-phenyl}-methanesulfonamide The title compound (48 mg) is prepared in analogy to Example 11 starting from 2-cyclopentyl-6-methoxy-isonicotinic acid (48 mg, 217 μmol) and 3-ethyl-N-hydroxy-4-methanesulfonylamino-5-methyl-benzamidine (62 mg, 228 mmol); LC-MS**: $t_R$=0.91 min, [M+H]$^+$=457.05; $^1$H NMR (CDCl$_3$): δ1.35 (t, J=7.5 Hz, 3H), 1.71-1.80 (m, 2H), 1.84-1.95 (m, 4H), 2.06-2.16 (m, 2H), 2.56 (s, 3H), 2.93 (q, J=7.5 Hz, 2H), 3.18 (s, 3H), 3.21-3.30 (m, 1H), 4.02 (s, 3H), 5.88 (s, 1H), 7.31 (s, 1H), 7.51 (s, 1H), 7.97 (s, 1H), 7.99 (s, 1H).

Example 20

N-{4-[5-(2-Cyclohexyl-6-methoxy-pyridin-4-yl)-[1,2,4]oxadiazol-3-yl]-2-ethyl-6-methyl-phenyl}-methanesulfonamide The title compound (7 mg) is prepared in analogy to Example 11 starting from 2-cyclohexyl-6-methoxy-isonicotinic acid (40 mg, 147 μmol) and 3-ethyl-N-hydroxy-4-methanesulfonylamino-5-methyl-benzamidine (42 mg, 155 mmol); LC-MS**: $t_R$=0.94 min, [M+H]$^+$=471.02; $^1$H NMR (CDCl$_3$): δ1.35 (t, J=7.8 Hz, 3H), 1.40-1.70 (m, 5H), 1.77-1.84 (m, 1H), 1.88-1.96 (m, 2H), 2.00-2.08 (m, 2H), 2.56 (s, 3H), 2.71-2.81 (m, 1H), 2.93 (q, J=7.0 Hz, 2H), 3.18 (s, 3H), 4.03 (s, 3H), 5.87 (s, 1H), 7.32 (s, 1H), 7.49 (s, 1H), 7.97 (s, 1H), 7.99 (s, 1H).

Example 21

(S)-3-{4-[3-(2-Cyclopentyl-6-methoxy-pyridin-4-yl)-[1,2,4]oxadiazol-5-yl]-2-ethyl-6-methyl-phenoxy}-propane-1,2-diol a) To a solution of 2-cyclopentyl-N-hydroxy-6-methoxy-isonicotinamidine (870 mg, 3.70 mmol), 4-benzyloxy-3-ethyl-5-methyl-benzoic acid (1.00 g, 3.70 mmol) and DIPEA (1.44 g, 11.1 mmol) in DCM (30 mL), TBTU (1.43 g, 4.44 mmol) is added. The mixture is stirred at rt for 1 h before diluted with EA (150 mL) and water (50 mL). The org. phase is separated, washed with sat. aq. NaHCO$_3$ solution (50 mL) followed by brine (50 mL), dried over MgSO$_4$, filtered and concentrated. The remaining pale brown oil is dissolved in dioxane (40 mL) and then stirred at 115° C. for 48 h. The solvent is evaporated and the crude product is purified by CC on silica gel eluting with heptane:EA 1:9 to give 4-[5-(4-benzyloxy-3-ethyl-5-methyl-phenyl)-[1,2,4]oxadiazol-3-yl]-2-cyclopentyl-6-methoxy-pyridine (1040 mg) as a pale yellow oil; LC-MS**: $t_R$=1.11 min, [M+H]$^+$=470.26.

b) Pd/C (150 mg, 10% Pd) is added to a solution of 4-[5-(4-benzyloxy-3-ethyl-5-methyl-phenyl)-[1,2,4]oxadiazol-3-yl]-2-cyclopentyl-6-methoxy-pyridine (1040 mg, 2.22 mmol) in THF (20 mL) and methanol (20 mL). The mixture is stirred under 1 bar of H$_2$ at rt for 24 h. The catalyst is removed by filtration and the filtrate is concentrated and dried to give 4-[3-(2-cyclopentyl-6-methoxy-pyridin-4-yl)-[1,2,4]oxadiazol-5-yl]-2-ethyl-6-methyl-phenol (672 mg) as an off-white solid; LC-MS**: $t_R$=0.97 min, [M+H]$^+$=380.27.

c) A mixture of 4-[3-(2-cyclopentyl-6-methoxy-pyridin-4-yl)-[1,2,4]oxadiazol-5-yl]-2-ethyl-6-methyl-phenol (150 mg, 395 μmol) and (S)-3-chloro-propane-1,2-diol (366 mg, 3.31 mmol) in isopropanol (4 mL) and 3 N aq. NaOH (1 mL) is stirred at 70° C. for 48 h. The mixture is diluted with EA (50 mL), washed with 1 M aq. NaOH solution (20 mL) followed by brine (20 mL), dried over MgSO$_4$, filtered and concentrated. The crude product is purified by prep. HPLC to give the title compound (95 mg) as a pale brown oil; LC-MS**: $t_R$=0.88 min, [M+H]$^+$=454.08; $^1$H NMR (CDCl$_3$): δ1.34 (t, J=7.0 Hz, 3H), 1.67-1.79 (m, 2H), 1.82-1.96 (m, 4H), 2.04-2.15 (m, 2H), 2.43 (s, 3H), 2.79 (q, J=7.0 Hz, 2H), 3.18-3.29 (m, 1H), 3.81-3.99 (m, 4H), 4.01 (s, 3H), 4.15-4.22 (m, 1H), 7.30 (s, 1H), 7.49 (s, 1H), 7.93 (s, 1H), 7.94 (s, 1H).

Example 22

(R)-3-{4-[3-(2-Cyclopentyl-6-methoxy-pyridin-4-yl)-[1,2,4]oxadiazol-5-yl]-2-ethyl-6-methyl-phenoxy}-propane-1,2-diol The title compound (66 mg) is obtained as an almost colourless oil in analogy to Example 21 starting from 4-[3-(2-cyclopentyl-6-methoxy-pyridin-4-yl)-[1,2,4]oxadiazol-5-yl]-2-ethyl-6-methyl-phenol (100 mg, 264 μmol) and (R)-3-chloro-propane-1,2-diol (244 mg, 2.21 mmol); LC-MS**: $t_R$=0.88 min, [M+H]$^+$=454.21.

Example 23

N-((2S)-3-{4-[3-(2-Cyclopentyl-6-methoxy-pyridin-4-yl)-[1,2,4]oxadiazol-5-yl]-2-ethyl-6-methyl-phenoxy}-2-hydroxy-propyl)-2-hydroxy-acetamide a) A mixture of 4-[3-(2-cyclopentyl-6-methoxy-pyridin-4-yl)-[1,2,4]oxadiazol-5-yl]-2-ethyl-6-methyl-phenol (150 mg, 395 µmol) and (R)-epichlorohydrine (366 mg, 3.95 mmol) in isopropanol (4 mL) and 3 N aq. NaOH (1 mL) is stirred at rt for 72 h. The mixture is diluted with EA (50 mL), washed with 1 M aq. NaOH solution (20 mL) followed by brine (20 mL), dried over MgSO$_4$, filtered and concentrated. The crude product is purified on prep. TLC plates using heptane:EA 1:1 to give 2-cyclopentyl-4-[5-((S)-3-ethyl-5-methyl-4-oxiranylmethoxy-phenyl)-[1,2,4]oxadiazol-3-yl]-6-methoxy-pyridine (96 mg) as a pale yellow oil; LC-MS**: $t_R$=1.02 min, [M+H]$^+$=436.18.

b) A solution of 2-cyclopentyl-4-[5-((S)-3-ethyl-5-methyl-4-oxiranylmethoxy-phenyl)-[1,2,4]oxadiazol-3-yl]-6-methoxy-pyridine (96 mg, 220 µmol) in 7 N NH$_3$ in methanol (5 mL) is stirred at 65° C. for 24 h. The mixture is evaporated and dried to give crude (2S)-1-amino-3-{4-[3-(2-cyclopentyl-6-methoxy-pyridin-4-yl)-[1,2,4]oxadiazol-5-yl]-2-ethyl-6-methyl-phenoxy}-propan-2-ol (101 mg) as a pale yellow oil; LC-MS**: $t_R$=0.72 min, [M+H]$^+$=453.27.

c) To a solution of (2S)-1-amino-3-{4-[3-(2-cyclopentyl-6-methoxy-pyridin-4-yl)-[1,2,4]oxadiazol-5-yl]-2-ethyl-6-methyl-phenoxy}-propan-2-ol (100 mg, 220 µmol), glycolic acid (22 mg, 289 µmol) and DIPEA (86 mg, 666 µmol) in DMF (3 mL), TBTU (93 mg, 289 µmol) is added. The mixture is stirred at rt for 1 h before it is diluted with EA (50 mL) and washed with sat. aq. NaHCO$_3$ solution (20 mL) followed by brine (20 mL). The org. extract is dried over MgSO$_4$, filtered and concentrated. The crude product is purified by prep. HPLC to give the title compound (65 mg) as an almost colourless oil; LC-MS**: $t_R$=0.84 min, [M+H]$^+$=511.03; $^1$H NMR (CDCL$_3$): δ1.33 (t, J=7.5 Hz, 3H), 1.68-1.79 (m, 2H), 1.82-1.95 (m, 4H), 2.05-2.15 (m, 2H), 2.41 (s, 3H), 2.76 (q, J=7.5 Hz, 2H), 3.18-3.28 (m, 1H), 3.49-3.59 (m, 1H), 3.75-3.95 (m, 3H), 4.01 (s, 3H), 4.18-4.26 (m, 3H), 7.08 (t, J=4.3 Hz, 1H), 7.49 (s, 1H), 7.91 (s, 1H), 7.93 (s, 1H).

Example 24

N-((2R)-3-{4-[3-(2-Cyclopentyl-6-methoxy-pyridin-4-yl)-[1,2,4]oxadiazol-5-yl]-2-ethyl-6-methyl-phenoxy}-2-hydroxy-propyl)-2-hydroxy-acetamide The title compound is prepared in analogy to Example 23 using (S)-epichlorohydrine; LC-MS**: $t_R$=0.84 min, [M+H]$^+$=511.27.

Example 25

(S)-3-{4-[5-(2-Cyclopentyl-6-methoxy-pyridin-4-yl)-[1,3,4]oxadiazol-2-yl]-2-ethyl-6-methyl-phenoxy}-propane-1,2-diol a) A solution of 2-cyclopentyl-6-methoxy-isonicotinic acid hydrazide (870 mg, 3.70 mmol), 4-benzyloxy-3-ethyl-5-methyl-benzoic acid (1.00 g, 3.70 mmol) and DIPEA (1.44 g, 11.1 mmol) in DCM (30 mL), TBTU (1.43 g, 4.44 mmol) is added. The mixture is stirred at rt for 1 h before it is diluted with EA (150 mL) and water (50 mL). The org. phase is separated, washed with sat. aq. NaHCO$_3$ solution (50 mL) followed by brine (50 mL), dried over MgSO$_4$, filtered and concentrated. The remaining pale yellow oil is dissolved in THF (50 mL) and Burgess reagent (1.23 g, 5.18 mmol) is added. The mixture is stirred at 110° C. for 15 min under microwave irradiation before it is diluted with EA (200 mL) and washed twice with water (50 mL). The org. extract is dried over MgSO$_4$, filtered and concentrated and the crude product is purified by CC on silica gel eluting with heptane:EA 1:9 to give 4-[5-(4-benzyloxy-3-ethyl-5-methyl-phenyl)-[1,3,4]oxadiazol-2-yl]-2-cyclopentyl-6-methoxy-pyridine (750 mg) as a pale yellow oil; LC-MS**: $t_R$=1.06 min, [M+H]$^+$=470.21.

b) Pd/C (150 mg, 10% Pd) is added to a solution of 4-[5-(4-benzyloxy-3-ethyl-5-methyl-phenyl)-[1,3,4]oxadiazol-2-yl]-2-cyclopentyl-6-methoxy-pyridine (750 mg, 1.60 mmol) in THF (20 mL) and methanol (20 mL). The mixture is stirred under 1 bar of H$_2$ at rt for 24 h. The catalyst is removed by filtration and the filtrate is concentrated and dried to give 4-[5-(2-cyclopentyl-6-methoxy-pyridin-4-yl)-[1,3,4]oxadiazol-2-yl]-2-ethyl-6-methyl-phenol (495 mg) as a white solid; LC-MS**: $t_R$=0.91 min, [M+H]$^+$=380.25; $^1$H NMR (D$_6$-DMSO): δ 1.20 (t, J=7.5 Hz, 3H), 1.65-1.74 (m, 2H), 1.76-1.88 (m, 4H), 1.99-2.09 (m, 2H), 2.29 (s, 3H), 2.69 (q, J=7.5 Hz, 2H), 3.94 (s, 3H), 7.26 (d, J=1.0 Hz, 1H), 7.50 (d, J=0.8 Hz, 1H), 7.76 (d, J=2.0 Hz, 1H), 7.78 (d, J=2.0 Hz, 1H).

c) A mixture of 4-[5-(2-cyclopentyl-6-methoxy-pyridin-4-yl)-[1,3,4]oxadiazol-2-yl]-2-ethyl-6-methyl-phenol (100 mg, 264 µmol) and (S)-3-chloro-propane-1,2-diol (244 mg, 2.64 mmol) in isopropanol (4 mL) and 3 N aq. NaOH (1 mL) is stirred at 70° C. for 48 h. The mixture is diluted with EA (50 mL), washed with 1 M aq. NaOH solution (20 mL) followed by brine (20 mL), dried over MgSO$_4$, filtered and concentrated. The crude product is purified by prep. HPLC to give the title compound (86 mg) as a white solid; LC-MS**: $t_R$=0.83 min, [M+H]$^+$=454.12; $^1$H NMR (CDCl$_3$): δ1.33 (t, J=7.5 Hz, 3H), 1.65-1.80 (m, 2H), 1.83-1.96 (m, 4H), 2.05-2.15 (m, 2H), 2.42 (s, 3H), 2.78 (q, J=7.3 Hz, 2H), 3.19-3.30 (m, 1H), 3.82-3.99 (m, 4H), 4.02 (s, 3H), 4.15-4.23 (m, 1H), 7.22 (s, 1H), 7.48 (s, 1H), 7.84 (s, 1H), 7.86 (s, 1H).

Example 26

(R)-3-{4-[5-(2-Cyclopentyl-6-methoxy-pyridin-4-yl)-[1,3,4]oxadiazol-2-yl]-2-ethyl-6-methyl-phenoxy}-propane-1,2-diol The title compound (40 mg) is obtained as a white solid starting from 4-[5-(2-cyclopentyl-6-methoxy-pyridin-4-yl)-[1,3,4]oxadiazol-2-yl]-2-ethyl-6-methyl-phenol (50 mg, 132 µmol) and (R)-3-chloro-propane-1,2-diol (122 mg, 1.32 mmol) in analogy to Example 25; LC-MS**: $t_R$=0.82 min, [M+H]$^+$=454.21.

Example 27

N-((2S)-3-{4-[5-(2-Cyclopentyl-6-methoxy-pyridin-4-yl)-[1,3,4]oxadiazol-2-yl]-2-ethyl-6-methyl-phenoxy}-2-hydroxy-propyl)-2-hydroxy-acetamide The title compound is prepared in analogy to Example 23 starting from 4-[5-(2-cyclopentyl-6-methoxy-pyridin-4-yl)-[1,3,4]oxadiazol-2-yl]-2-ethyl-6-methyl-phenol and (R)-epichlorohydrine; LC-MS**: $t_R$=0.79 min, [M+H]$^+$=511.16; $^1$H NMR (CDCl$_3$): δ1.32 (t, J=7.3 Hz, 3H), 1.68-1.79 (m, 2H), 1.80-1.95 (m, 4H), 2.05-2.15 (m, 2H), 2.40 (s, 3H), 2.76 (q, J=7.5 Hz, 2H), 3.18-3.28 (m, 1H), 3.49-3.59 (m, 1H), 3.76-3.94 (m, 3H), 4.01 (s, 3H), 4.19-4.27 (m, 3H), 7.10 (t br, J=5.8 Hz, 1H), 7.21 (s, 1H), 7.47 (s, 1H), 7.83 (s, 1H), 7.85 (s, 1H).

Example 28

N-((2R)-3-{4-[5-(2-Cyclopentyl-6-methoxy-pyridin-4-yl)-[1,3,4]oxadiazol-2-yl]-2-ethyl-6-methyl-phenoxy}-2-hydroxy-propyl)-2-hydroxy-acetamide The title compound is prepared in analogy to Example 23 starting from 4-[5-(2-cyclopentyl-6-methoxy-pyridin-4-yl)-[1,3,4]oxadiazol-2-yl]-2-ethyl-6-methyl-phenol and (S)-epichlorohydrine; LC-MS**: $t_R$=0.79 min, [M+H]$^+$=511.24.

Example 29

(S)-3-{2-Chloro-4-[5-(2-cyclohexyl-6-methoxy-pyridin-4-yl)-[1,2,4]oxadiazol-3-yl]-6-methyl-phenoxy}-propane-1,2-diol The title compound is prepared in analogy to Example 3 starting from 2-cyclohexyl-6-methoxy-isonicotinic acid, 3-chloro-4,N-dihydroxy-5-methyl-benzamidine and (S)-3-chloro-1,2-propanediol; LC-MS**: $t_R$=1.01 min, [M+H]$^+$=473.95; $^1$H NMR (CDCl$_3$): δ: 8.08 (s, 1H), 7.94 (s, 1H), 7.48 (s, 1H), 7.30 (s, 1H), 4.18 (m, 1H), 4.10-4.14 (m, 2H), 4.03 (s, 3H), 3.84-3.95 (m, 2H), 2.84 (s br, 1H), 2.69-2.80 (m, 1H), 2.45 (s, 3H), 1.99-2.13 (m, 2H), 1.86-1.96 (m, 2H), 1.76-1.84 (m, 1H), 1.15-1.68 (m, 6H).

Example 30

N-(2-Ethyl-4-(5-(2-isopentyl-6-methoxypyridin-4-yl)-1,2,4-oxadiazol-3-yl)-6-methylphenyl)methanesulfonamide The title compound is obtained as a white solid (85 mg) in analogy to Example 11 starting from 2-methoxy-6-(3-methyl-butyl)-isonicotinic acid (131 mg, 0.587 mmol) and 3-ethyl-N-hydroxy-4-methanesulfonylamino-5-methyl-benzamidine (186 mg, 0.616 mmol); LC-MS**: $t_R$=1.07 min, [M+H]$^+$=459.23; $^1$H NMR (D$_6$-DMSO): δ: 9.07 (s, 1H), 7.85 (s, 2H), 7.57 (s, 1H), 7.30 (s, 1H), 3.95 (s, 3H), 3.13 (s, 3H), 2.79-2.90 (m, 4H), 2.47 (s, 3H), 1.58-1.68 (m, 3H), 1.23 (t, J=7.5 Hz, 3H), 0.95 (d, J=6.2 Hz, 6H).

Example 31

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order#6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Agonistic activities (EC$_{50}$ values) of all exemplified compounds have been measured. EC$_{50}$ values of these compounds are displayed in Table 2.

TABLE 2

| Compound of Example | EC$_{50}$ [nM] |
| --- | --- |
| 1 | 2.7 |
| 2 | 0.9 |
| 3 | 1.0 |
| 4 | 6.4 |
| 5 | 1.8 |
| 6 | 0.6 |
| 7 | 0.6 |
| 8 | 10.8 |
| 9 | 17.8 |
| 10 | 2.6 |
| 11 | 1.2 |
| 12 | 0.3 |
| 13 | 1.0 |
| 14 | 1.1 |
| 15 | 7.5 |
| 16 | 0.7 |
| 17 | 10.2 |
| 18 | 2.5 |
| 19 | 1.0 |
| 20 | 4.2 |
| 21 | 0.7 |
| 22 | 1.0 |
| 23 | 0.4 |
| 24 | 1.6 |
| 25 | 1.9 |
| 26 | 4.0 |
| 27 | 1.7 |
| 28 | 2.3 |
| 29 | 4.0 |
| 30 | 5.6 |

Example 32

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 3 shows the effect on lymphocyte counts 6 h after oral administration of 10 mg/kg of a compound of the present invention to normotensive male Wistar rats as compared to a group of animals treated with vehicle only. Lymphocyte counts 6 h after oral administration have been measured for 23 out of 30 exemplified compounds and are in the range of −42% to −80% with an average of −63%.

TABLE 3

| Compound of Example | Lymphocyte counts |
|---|---|
| 1 | −63% |
| 2 | −70% |
| 3 | −63% |
| 4 | −61% |
| 5 | −66% |
| 6 | −59% |
| 7 | −65% |
| 8 | −58% |
| 10 | −68% |
| 11 | −74% |
| 12 | −64% |
| 13 | −60% |
| 14 | −70% |
| 16 | −73% |
| 17 | −80% |
| 18 | −42% |
| 19 | −61% |
| 20 | −67% |
| 21 | −62% |
| 23 | −56% |
| 25 | −51% |
| 27 | −54% |
| 29 | −62% |

Example 33

Measurement of Isometric Force Development

Animals were obtained from RCC Ltd (Füllinsdorf, Switzerland). Female Wistar rats were euthanized by exposure to $CO_2$. The tracheae were excised and rings from the lower segments were prepared. Rings of trachea were suspended in tissue baths (10 mL) containing Krebs-Henseleit buffer of the following composition (mM): NaCl 115; KCl 4.7; $MgSO_4$ 1.2; $KH_2PO_4$ 1.5; $CaCl_2$ 2.5; $NaHCO_3$ 25; glucose 10. Bathing solution was maintained at 37° C. and aerated with 95% $O_2$/5% $CO_2$ (pH 7.4). A resting force of 2 g (20 mN) was applied to the ring preparation, and changes in force generation were measured using an isometric force recorder (EMKA Technologies Inc, Paris, France). Viability of rings was assessed by exposure to a depolarizing concentration of KCl (50 mM). Contraction of trachea was expressed as a percentage of the response to KCl.

All compounds were prepared as stock solutions of 0.3 mM in pure DMSO. Compounds were added to the bath (10 mL) in a volume of 33 μL to give a final bath concentration of DMSO of 0.33%.

Contraction of trachea was measured for 15 out of 30 exemplified compounds. The results are compiled in Table 4.

TABLE 4

| Compound | % trachea constriction | |
|---|---|---|
|  | at 1 μM | at 10 μM |
| Example 1 | <5 | 24 |
| Example 2 | <5 | <5 |
| Example 3 | <5 | n.d. |
| Example 4 | <5 | n.d. |
| Example 6 | <5 | 100 |
| Example 7 | 50 | n.d. |
| Example 8 | <5 | n.d. |
| Example 10 | <5 | <5 |
| Example 12 | <5 | <5 |
| Example 13 | <5 | n.d. |
| Example 16 | <5 | n.d. |
| Example 18 | <5 | <5 |
| Example 19 | <5 | <5 |

TABLE 4-continued

| Compound | % trachea constriction | |
|---|---|---|
|  | at 1 μM | at 10 μM |
| Example 21 | <5 | n.d. |
| Example 25 | 53 | n.d. |

The invention claimed is:

1. A compound of the Formula (I),

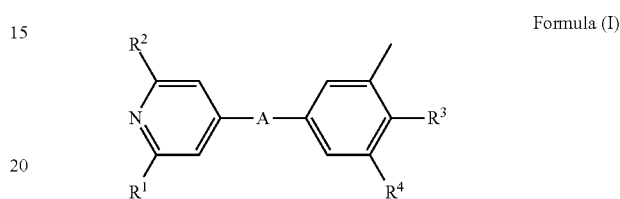

Formula (I)

wherein

A represents

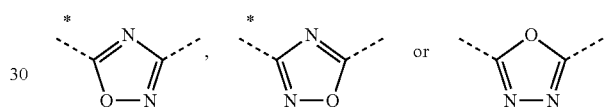

wherein the asterisks indicate the bond that is linked to the pyridine group of Formula (I);

$R^1$ represents 3-pentyl, 3-methyl-but-1-yl, cyclopentyl, or cyclohexyl;

$R^2$ represents methoxy;

$R^3$ represents 2,3-dihydroxypropoxy, —$OCH_2$—CH(OH)—$CH_2$—NHCO—$CH_2$OH, —$OCH_2$—CH(OH)—$CH_2$N($CH_3$)—CO—$CH_2$OH, —$NHSO_2CH_3$, or —$NHSO_2CH_2CH_3$; and $R^4$ represents ethyl or chloro;

or salts thereof.

2. A compound according to claim 1, wherein the stereocenter of the $R^3$ groups 2,3-dihydroxypropoxy, —$OCH_2$—CH(OH)—$CH_2$—NHCO—$CH_2$OH, and —$OCH_2$—CH(OH)—$CH_2$N($CH_3$)—CO—$CH_2$OH is in the S-configuration, or salts thereof.

3. A compound according to claim 1, wherein the stereocenter of the $R^3$ groups 2,3-dihydroxypropoxy, —$OCH_2$—CH(OH)—$CH_2$—NHCO—$CH_2$OH, and —$OCH_2$—CH(OH)—$CH_2$N($CH_3$)—CO—$CH_2$OH is in the R-configuration, or salts thereof.

4. A compound according to claim 1, wherein A represents

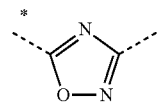

wherein the asterisk indicates the bond that is linked to the pyridine group of Formula (I), or salts thereof.

5. A compound according to claim 1, wherein A represents

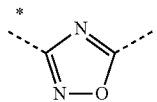

wherein the asterisk indicates the bond that is linked to the pyridine group of Formula (I), or salts thereof.

6. A compound according to claim 1, wherein A represents

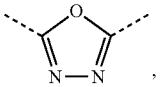

or salts thereof.

7. A compound according to claim 1, wherein $R^1$ represents 3-pentyl, or salts thereof.

8. A compound according to claim 1, wherein $R^1$ represents 3-methyl-but-1-yl, or salts thereof.

9. A compound according to claim 1, wherein $R^1$ represents cyclopentyl, or salts thereof.

10. A compound according to claim 1, wherein $R^1$ represents cyclohexyl, or salts thereof.

11. A compound according to claim 1, wherein $R^3$ represents 2,3-dihydroxypropoxy, or salts thereof.

12. A compound according to claim 1, wherein $R^3$ represents —OCH$_2$—CH(OH)—CH$_2$—NHCO—CH$_2$OH, or salts thereof.

13. A compound according to claim 1, wherein $R^3$ represents —OCH$_2$—CH(OH)—CH$_2$N(CH$_3$)—CO—CH$_2$OH, or salts thereof.

14. A compound according to claim 1, wherein $R^3$ represents —NHSO$_2$CH$_3$, or salts thereof.

15. A compound according to claim 1, wherein $R^3$ represents —NHSO$_2$CH$_2$CH$_3$, or salts thereof.

16. A compound according to claim 1, wherein $R^4$ represents ethyl, or salts thereof.

17. A compound according to claim 1, wherein $R^4$ represents chloro, or salts thereof.

18. A compound according to claim 1 selected from the group consisting of:
- (S)-3-(2-Ethyl-4-{5-[2-(1-ethyl-propyl)-6-methoxy-pyridin-4-yl]-[1,2,4]oxadiazol-3-yl}-6-methyl-phenoxy)-propane-1,2-diol;
- (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol;
- (R)-3-{4-[5-(2-cyclopentyl-6-methoxy-pyridin-4-yl)-[1,2,4]oxadiazol-3-yl]-2-ethyl-6-methyl-phenoxy}-propane-1,2-diol;
- (S)-3-{4-[5-(2-cyclohexyl-6-methoxy-pyridin-4-yl)-[1,2,4]oxadiazol-3-yl]-2-ethyl-6-methyl-phenoxy}-propane-1,2-diol;
- ethanesulfonic acid {2-chloro-4-[5-(2-cyclopentyl-6-methoxy-pyridin-4-yl)-[1,2,4]oxadiazol-3-yl]-6-methyl-phenyl}-amide;
- N—[(S)-3-(2-ethyl-4-{5-[2-(1-ethyl-propyl)-6-methoxy-pyridin-4-yl]-[1,2,4]oxadiazol-3-yl}-6-methyl-phenoxy)-2-hydroxy-propyl]-2-hydroxy-acetamide;
- N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-acetamide;
- N—((S)-3-{4-[5-(2-cyclohexyl-6-methoxy-pyridin-4-yl)-[1,2,4]oxadiazol-3-yl]-2-ethyl-6-methyl-phenoxy}-2-hydroxy-propyl)-2-hydroxy-acetamide;
- N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide;
- N-(2-chloro-4-{5-[2-(1-ethyl-propyl)-6-methoxy-pyridin-4-yl]-[1,2,4]oxadiazol-3-yl}-6-methyl-phenyl)-methanesulfonamide;
- N-{2-chloro-4-[5-(2-cyclopentyl-6-methoxy-pyridin-4-yl)-[1,2,4]oxadiazol-3-yl]-6-methyl-phenyl}-methanesulfonamide;
- (S)-3-{2-chloro-4-[5-(2-cyclopentyl-6-methoxy-pyridin-4-yl)-[1,2,4]oxadiazol-3-yl]-6-methyl-phenoxy}-propane-1,2-diol;
- N—((S)-3-{2-chloro-4-[5-(2-cyclopentyl-6-methoxy-pyridin-4-yl)-[1,2,4]oxadiazol-3-yl]-6-methyl-phenoxy}-2-hydroxy-propyl)-2-hydroxy-acetamide;
- (S)-3-(2-ethyl-4-{5-[2-methoxy-6-(3-methyl-butyl)-pyridin-4-yl]-[1,2,4]oxadiazol-3-yl}-6-methyl-phenoxy)-propane-1,2-diol;
- N—[(S)-3-(2-ethyl-4-{5-[2-methoxy-6-(3-methyl-butyl)-pyridin-4-yl]-[1,2,4]oxadiazol-3-yl}-6-methyl-phenoxy)-2-hydroxy-propyl]-2-hydroxy-acetamide;
- N-{2-chloro-4-[5-(2-cyclohexyl-6-methoxy-pyridin-4-yl)-[1,2,4]oxadiazol-3-yl]-6-methyl-phenyl}-methanesulfonamide;
- N-(2-ethyl-4-{5-[2-(1-ethyl-propyl)-6-methoxy-pyridin-4-yl]-[1,2,4]oxadiazol-3-yl}-6-methyl-phenyl)-methanesulfonamide;
- N-{4-[5-(2-cyclopentyl-6-methoxy-pyridin-4-yl)-[1,2,4]oxadiazol-3-yl]-2-ethyl-6-methyl-phenyl}-methanesulfonamide;
- N-{4-[5-(2-cyclohexyl-6-methoxy-pyridin-4-yl)-[1,2,4]oxadiazol-3-yl]-2-ethyl-6-methyl-phenyl}-methanesulfonamide;
- (S)-3-{4-[3-(2-cyclopentyl-6-methoxy-pyridin-4-yl)-[1,2,4]oxadiazol-5-yl]-2-ethyl-6-methyl-phenoxy}-propane-1,2-diol;
- (R)-3-{4-[3-(2-cyclopentyl-6-methoxy-pyridin-4-yl)-[1,2,4]oxadiazol-5-yl]-2-ethyl-6-methyl-phenoxy}-propane-1,2-diol;
- N—((S)-3-{4-[3-(2-cyclopentyl-6-methoxy-pyridin-4-yl)-[1,2,4]oxadiazol-5-yl]-2-ethyl-6-methyl-phenoxy}-2-hydroxy-propyl)-2-hydroxy-acetamide;
- N—((R)-3-{4-[3-(2-cyclopentyl-6-methoxy-pyridin-4-yl)-[1,2,4]oxadiazol-5-yl]-2-ethyl-6-methyl-phenoxy}-2-hydroxy-propyl)-2-hydroxy-acetamide;
- (S)-3-{4-[5-(2-cyclopentyl-6-methoxy-pyridin-4-yl)-[1,3,4]oxadiazol-2-yl]-2-ethyl-6-methyl-phenoxy}-propane-1,2-diol;
- (R)-3-{4-[5-(2-cyclopentyl-6-methoxy-pyridin-4-yl)-[1,3,4]oxadiazol-2-yl]-2-ethyl-6-methyl-phenoxy}-propane-1,2-diol;
- N—((S)-3-{4-[5-(2-cyclopentyl-6-methoxy-pyridin-4-yl)-[1,3,4]oxadiazol-2-yl]-2-ethyl-6-methyl-phenoxy}-2-hydroxy-propyl)-2-hydroxy-acetamide; and
- N—((R)-3-{4-[5-(2-cyclopentyl-6-methoxy-pyridin-4-yl)-[1,3,4]oxadiazol-2-yl]-2-ethyl-6-methyl-phenoxy}-2-hydroxy-propyl)-2-hydroxy-acetamide;

or salts of these compounds.

19. A compound according to claim 1 selected from the group consisting of:
- (S)-3-{2-chloro-4-[5-(2-cyclohexyl-6-methoxy-pyridin-4-yl)-[1,2,4]oxadiazol-3-yl]-6-methyl-phenoxy}-propane-1,2-diol; and N-(2-ethyl-4-(5-(2-isopentyl-6-methoxypyridin-4-yl)-1, 2,4-oxadiazol-3-yl)-6-methylphenyl)methanesulfonamide;

or salts of these compounds.

20. A pharmaceutical composition comprising a compound according to claim 1, or a pharmaceutically acceptable salt thereof, and a pharmaceutically acceptable carrier.

21. A method for the treatment of diseases or disorders associated with an activated immune system comprising administering the compound of claim 1, or a pharmaceutically acceptable salt thereof, to a patient in need thereof.

22. The method of claim 21, wherein the diseases or disorders is selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis.

23. The compound according to claim 1 which is (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol or a salt thereof.

24. The compound according to claim 1 which is N-((2S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide or a salt thereof.

25. The compound according to claim 1 which is N-{2-chloro-4-[5-(2-cyclopentyl-6-methoxy-pyridin-4-yl)-[1,2,4]oxadiazol-3-yl]-6-methyl-phenyl}-methanesulfonamide or a salt thereof.

26. The compound according to claim 1 which is N-{4-[5-(2-cyclopentyl-6-methoxy-pyridin-4-yl)-[1,2,4]oxadiazol-3-yl]-2-ethyl-6-methyl-phenyl}-methanesulfonamide or a salt thereof.

27. The pharmaceutical composition according to claim 20, wherein the compound according to claim 1 is (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol or a pharmaceutically acceptable salt thereof.

28. The pharmaceutical composition according to claim 20, wherein the compound according to claim 1 is N-((2S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide or a pharmaceutically acceptable salt thereof.

29. The pharmaceutical composition according to claim 20, wherein the compound according to claim 1 is N-{2-chloro-4-[5-(2-cyclopentyl-6-methoxy-pyridin-4-yl)-[1,2,4]oxadiazol-3-yl]-6-methyl-phenyl}-methanesulfonamide or a pharmaceutically acceptable salt thereof.

30. The pharmaceutical composition according to claim 20, wherein the compound according to claim 1 is N-{4-[5-(2-cyclopentyl-6-methoxy-pyridin-4-yl)-[1,2,4]oxadiazol-3-yl]-2-ethyl-6-methyl-phenyl}-methanesulfonamide or a pharmaceutically acceptable salt thereof.

31. The method according to claim 22, wherein the compound according to claim 1 is (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol or a pharmaceutically acceptable salt thereof.

32. The method according to claim 22, wherein the compound according to claim 1 is N-((2S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide or a pharmaceutically acceptable salt thereof.

33. The method according to claim 22, wherein the compound according to claim 1 is N-{2-chloro-4-[5-(2-cyclopentyl-6-methoxy-pyridin-4-yl)-[1,2,4]oxadiazol-3-yl]-6-methyl-phenyl}-methanesulfonamide or a pharmaceutically acceptable salt thereof.

34. The method according to claim 22, wherein the compound according to claim 1 is N-{4-[5-(2-cyclopentyl-6-methoxy-pyridin-4-yl)-[1,2,4]oxadiazol-3-yl]-2-ethyl-6-methyl-phenyl}-methanesulfonamide or a pharmaceutically acceptable salt thereof.

35. A method for the prevention of graft-versus-host diseases brought about by stem cell transplantation or rejection of transplanted organs selected from the group consisting of kidney, liver, heart, lung, pancreas, cornea, and skin, comprising administering the compound of claim 1, or a pharmaceutically acceptable salt thereof, to a patient in need thereof.

36. A method for decreasing the number of circulating lymphocytes in a patient in need thereof comprising administering to said patient the compound according to claim 1, or a pharmaceutically acceptable salt thereof.

37. The method according to claim 36, wherein said patient is suffering from a disease or disorder associated with an activated immune system.

38. The method according to claim 37, wherein the compound according to claim 1 is (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol or a pharmaceutically acceptable salt thereof.

39. The method according to claim 37, wherein the compound according to claim 1 is N-((2S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide or a pharmaceutically acceptable salt thereof.

40. The method according to claim 37, wherein the compound according to claim 1 is N-{2-chloro-4-[5-(2-cyclopentyl-6-methoxy-pyridin-4-yl)-[1,2,4]oxadiazol-3-yl]-6-methyl-phenyl}-methanesulfonamide or a pharmaceutically acceptable salt thereof.

41. The method according to claim 37, wherein the compound according to claim 1 is N-{4-[5-(2-cyclopentyl-6-methoxy-pyridin-4-yl)-[1,2,4]oxadiazol-3-yl]-2-ethyl-6-methyl-phenyl}-methanesulfonamide or a pharmaceutically acceptable salt thereof.

42. The method according to claim 21, wherein the compound according to claim 1 is
(S)-3-{4-[5-(2-cyclopentyl-6-methoxy-pyridin-4-yl)-[1,2,4]oxadiazol-3-yl]-2-ethyl-6-methyl-phenoxy}-propane-1,2-diol or a pharmaceutically acceptable salt thereof.

43. The method according to claim 21, wherein the compound according to claim 1 is N-((2S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-2-hydroxy-N-methyl-acetamide or a pharmaceutically acceptable salt thereof.

44. The method according to claim 21, wherein the compound according to claim 1 is N-{2-chloro-4-[5-(2-cyclopentyl-6-methoxy-pyridin-4-yl)-[1,2,4]oxadiazol-3-yl]-6-methyl-phenyl}-methanesulfonamide or a pharmaceutically acceptable salt thereof.

45. The method according to claim 21, wherein the compound according to claim 1 is N-{4-[5-(2-cyclopentyl-6-methoxy-pyridin-4-yl)-[1,2,4]oxadiazol-3-yl]-2-ethyl-6-methyl-phenyl}-methanesulfonamide or a pharmaceutically acceptable salt thereof.

* * * * *

UNITED STATES PATENT AND TRADEMARK OFFICE
CERTIFICATE OF CORRECTION

PATENT NO. : 8,658,675 B2
APPLICATION NO. : 13/383619
DATED : February 25, 2014
INVENTOR(S) : Bolli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 40 days.

Signed and Sealed this

Twenty-ninth Day of September, 2015

Michelle K. Lee
*Director of the United States Patent and Trademark Office*